(12) United States Patent
Tatsuno et al.

(10) Patent No.: US 6,805,665 B1
(45) Date of Patent: Oct. 19, 2004

(54) IMAGE PICK-UP DEVICE FOR ENDOSCOPES

(75) Inventors: Yutaka Tatsuno, Sagamihara (JP); Fuminori Tanahashi, Shirakawa (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 09/890,175

(22) PCT Filed: Sep. 25, 2000

(86) PCT No.: PCT/JP00/06605

§ 371 (c)(1),
(2), (4) Date: Jul. 26, 2001

(87) PCT Pub. No.: WO01/41631

PCT Pub. Date: Jun. 14, 2001

(30) Foreign Application Priority Data

Dec. 9, 1999 (JP) .......................................... 11-350581

(51) Int. Cl.[7] ................................................ A61B 1/04
(52) U.S. Cl. ...................... 600/112; 600/101; 600/109; 600/110
(58) Field of Search ................. 600/109–112, 160–178; 348/65, 73

(56) References Cited

U.S. PATENT DOCUMENTS

| | | | | |
|---|---|---|---|---|
| 5,575,757 A | * | 11/1996 | Kennedy et al. | 600/167 |
| 5,577,991 A | * | 11/1996 | Akui et al. | 600/109 |
| 5,587,736 A | * | 12/1996 | Walls | 600/101 |
| 5,706,143 A | * | 1/1998 | Hipp | 126/4 |
| 5,797,836 A | * | 8/1998 | Lucey et al. | 600/109 |
| 5,836,867 A | * | 11/1998 | Speier et al. | 600/109 |
| 5,868,664 A | * | 2/1999 | Speier et al. | 600/101 |
| 6,030,339 A | * | 2/2000 | Tatsuno et al. | 600/112 |
| 6,080,101 A | * | 6/2000 | Tatsuno et al. | 600/109 |
| 6,346,073 B1 | * | 2/2002 | Thompson | 600/167 |
| 6,398,724 B1 | * | 6/2002 | May et al. | 600/167 |
| 6,547,721 B1 | * | 4/2003 | Higuma et al. | 600/133 |

FOREIGN PATENT DOCUMENTS

| | | | |
|---|---|---|---|
| JP | 2-87110 | 3/1990 | |
| JP | 10-179505 | 7/1998 | |
| JP | 11-216102 A | * 8/1999 | ............ A61B/1/00 |

OTHER PUBLICATIONS

English language abstract of Japanese Publication No. 11–216102, dated Aug. 10, 1999; and.

English language abstract of Japanese Publication No. 06–209904, dated Aug. 2, 1994.

* cited by examiner

*Primary Examiner*—John P Leubecker
*Assistant Examiner*—Henry M Johnson, III
(74) *Attorney, Agent, or Firm*—Scully, Scott, Murphy & Presser

(57) ABSTRACT

An imaging unit for endoscopes including optical elements for forming an optical image; an imaging device for photo-electrically converting the optical image; a hermetic seal member having at least said optical element and the imaging device incorporated therein; and an imaging device driver making it possible to arbitrarily adjust the position of the imaging device relative to the optical element from outside the hermetic seal member.

3 Claims, 12 Drawing Sheets

IMAGE PICK-UP DEVICE FOR ENDOSCOPES

TECHNICAL FIELD

The present invention relates to an imaging unit for endoscopes capable of being autoclaved with an imaging device incorporated therein while being mounted in an endoscope.

BACKGROUND ART

Recently, when an optical endoscope is used to optically propagate an optical image to a proximal part thereof by way of relay lenses or the like, an imaging unit for endoscopes is generally adopted to pick up the optical image so as to convert it into an electric signal. This is intended to display the optical image formed by the endoscope on a monitor or to store the optical image in an image recording apparatus.

This type of imaging unit for endoscopes comprises a focusing lens and an imaging device such as a charge-coupled device (CCD). The focusing lens has an optical image, which is propagated from an eyepiece unit in an endoscope, converged thereon. The imaging device picks up the optical image converged on the focusing lens. For successfully successfully picking up an optical image, the focusing lens and imaging device must be aligned with each other. For accomplishing the alignment, the imaging device and focusing lens must be aligned with each other in optical-axis directions and in directions of eccentricity (focusing mechanism), that is, directions perpendicular to the optical axis (eccentricity adjusting mechanism). The alignment in the optical-axis directions is achieved by optimizing a distance between the imaging device and focusing lens.

For example, Japanese Unexamined Patent Publication No. 2-87110 has proposed an imaging unit that includes as separate apparatuses a camera adaptor in which an image formation optical system is incorporated and a camera head in which an imaging device is incorporated. A focusing mechanism and an eccentricity adjusting mechanism are included for adjusting the positions of various optical systems.

In recent years, what is referred to as autoclaving has been adopted as an inexpensive sterilizing method for sterilizing an imaging unit for endoscopes. According to the autoclaving method, an object of sterilization.is left intact within high-pressure steam for a certain period of time. When it says that an imaging unit for endoscopes resists autoclaving, the imaging unit must have a focusing lens and an imaging device sealed hermetically.

However, the imaging unit for endoscopes described in the Japanese Unexamined Patent Publication No. 2-87110 must include the focusing adjusting mechanism and eccentricity adjusting mechanism. It is therefore hard to hermetically seal the movable components included in an adjusting mechanism while keeping the imaging unit resistive to autoclaving.

For example, Japanese Unexamined Patent Publication No. 10-258034 has proposed an imaging unit for endoscopes in which a focusing method that enables autoclaving is implemented and a means for driving a motor-driven aperture stop unit is incorporated.

However, the imaging unit for endoscopes described in the Japanese Unexamined Patent Publication No. 10-258034 must have an adaptor and a camera head detached from each other before being autoclaved. After the autoclaving is completed, when the imaging unit for endoscopes is reused, the adaptor and camera head must be attached to each other again. This is annoying. If this procedure is ignored, steam remaining in the adaptor and camera head may condense to blur an optical image.

Moreover, an aperture stop unit helpful in improving a depth of focus, which permits an optical image propagated from an eyepiece unit 13 in an endoscope that offers a small depth of focus to be observed clearly, includes a rotational driving structure. In efforts to reduce the size of the aperture stop unit, a focusing lens is incorporated in the rotational driving structure. Therefore, when the focusing lens must be movable, the aperture stop unit must be made larger in size or the diameter (effective diameter) of the lens must be made smaller. Otherwise, a mechanism for moving the focusing lens along the optical axis of an optical system including the focusing lens must be included in the aperture stop unit. Otherwise, the camera head must be made larger in size in order to interpose another focusing lens between the aperture stop unit and imaging device. In this case, if an engagement length along the optical axis of the camera head is set to a length required for suppressing the tilt of the focusing lens, the camera head becomes very large. This poses a problem. Furthermore, since a hermetic connector is required in order to mount the aperture stop unit, the camera head becomes structurally complex, large in size, and costly.

In contrast, Japanese Unexamined Patent Publication No. 10-179505 has proposed an imaging unit for endoscopes in which a lens and an imaging device are integrated with each other. Herein, magnets are used to drive the lens for focusing.

However, the imaging unit for endoscopes described in the Japanese Unexamined Patent Publication No. 10-179505 cannot adjust eccentricity after a hermetic seal member is constructed. Moreover, magnetic coupling force has limitations (for increasing the force, it is necessary to extend the distance between the north and south poles of each of paired magnets or to increase the number of pairs of magnets). When measures are taken in order to intensify the magnetic coupling force, frictional resistance occurring on a sliding surface increases. This necessitates a clearance between a lens barrel and a locking frame. The clearance results in a displacement of a view image. A known countermeasure is employment of an elastic member. However, the magnetic coupling force must be further intensified in order to cancel constraining force exerted by the elastic member. Consequently, eccentricity of an optical image cannot be suppressed any longer.

In the imaging unit for endoscopes described in the Japanese Unexamined Patent Publication No. 10-258034, the adaptor and camera head are detached from each other before autoclaving. After the autoclaving is completed, when the imaging unit for endoscopes is reused, the adaptor and camera head must be attached to each other. This handling annoys a user. Moreover, the aperture stop unit includes the rotational driving structure in which the focusing lens is incorporated for the purpose of realizing a compact design. Therefore, when the lens must be movable, a mechanism for moving the lens along the optical axis must be included in the aperture stop unit. Otherwise, the camera head must be made larger in size in order to interpose another focusing lens between the aperture stop unit and imaging device. In this case, if an engagement length along the optical axis of the camera head is set to a length suppressing the tilt of the lens, the camera head must be made very large. Besides, a hermetic connector is required in order to mount the aperture stop unit. Therefore, the imaging unit becomes structurally complex, large in size, and costly.

On the other hand, in the imaging unit for endoscopes described in the Japanese Unexamined Patent Publication No. 10-179505, after the hermetic seal member is constructed, eccentricity cannot be adjusted. Moreover, the magnetic coupling force has limitations. When measures are taken to intensity the force, frictional resistance occurring on a sliding surface increases. Consequently, a clearance must be preserved between the lens barrel and locking frame. The clearance results in a displacement of a view image. When an elastic member is included as a countermeasure, the magnetic coupling force must be further intensified in order to cancel constraining force exerted by the elastic member. Consequently, eccentricity of an optical image cannot be suppressed.

The present invention attempts to break through the foregoing situation. An object of the present invention is to provide an imaging unit for endoscopes capable of being autoclaved without the necessity of dismounting optical elements and an imaging device. Moreover, the imaging unit for endoscopes offers excellent maneuverability. Furthermore, the position of the imaging device relative to the optical elements can be adjusted with the imaging unit kept hermetic.

In an optical system adjusting mechanism included in a conventional imaging unit for endoscopes which has been disclosed in, for example, Japanese Examined Patent Publication No. 4-58753, a turning pair that can be turned with the imaging surface of an imaging device as a center of rotation is realized using a frame. The position of the imaging device along the optical axis of an optical system including the imaging unit is adjustable.

According to Japanese Unexamined Patent Publication No. 2-289225, a turning pair is included, and a lens barrel is made movable arbitrarily along the optical axis of an optical system.

According to Japanese Examined Patent Publication NO. 4-58753, a mechanism for adjusting a swing (eccentricity) of an imaging device and adjusting the position of the imaging device relative to an optical system includes a turning pair whose center is aligned with the center of the imaging surface of the imaging device. The mechanism is effective in adjusting the swing. The imaging device and a frame that holds the imaging device can be moved in optical-axis directions.

According to Japanese Unexamined Patent Publication No. 2289225, a unit cylinder that bears an imaging device includes a turning pair and enables adjustment of a swing. Although an operator can finely adjust an optical system, the operator is not permitted to arbitrarily adjust the imaging device itself Furthermore, it is impossible to prevent invasion of high-pressure steam generated during autoclaving.

For example, Japanese Unexamnined Patent Publication No. 10-179505 has disclosed an art that a lens and an imaging device are integrated with each other and stowed in a hermetic frame. The lens is driven externally using magnets, whereby focusing is achieved. According to the related art, since the lens and imaging device are stowed in the hermetic frame, even when autoclaving is performed, high-pressure steam will not invade into the hermetic frame.

DISCLOSURE OF INVENTION

For accomplishing the above object, a first imaging unit for endoscopes in accordance with the present invention consists mainly of optical elements, an imaging device, a hermetic seal member, and an imaging device driving means. The optical elements form an optical image. The imaging device photoelectrically converts the optical image. The hermetic seal member has at least the optical element and the imaging device incorporated therein. The imaging device driving means makes it possible to arbitrarily adjust the position of the imaging device relative to the optical elements from outside the hermetic seal member.

A second imaging unit for endoscopes is identical to the first imaging unit for endoscopes except that the imaging device driving means is an eccentricity adjusting means for adjusting eccentricity of the imaging device relative to the optical axis of the optical elements.

A third imaging unit for endoscopes is identical to the first imaging unit for endoscopes except that the imaging device driving means is a focusing means that moves the optical elements and imaging device along the optical axis.

A fourth imaging unit for endoscopes is identical to the third imaging unit for endoscopes except that the image plane of the imaging device is located substantially in the middle of an engagement length of a frame, which holds the imaging device, along the optical axis.

A fifth imaging unit for endoscopes is identical to the first imaging unit for endoscopes except that the imaging device driving means is an adjusting means that rotates the imaging device with the optical axis of the optical elements as a center.

Consequently, at least the optical elements and the imaging device are stowed in the hermetic seal member. The eccentricity of the imaging device relative to the optical elements is adjusted from outside the hermetic seal member, and focusing is performed from outside the hermetic seal member. The imaging unit can therefore be autoclaved without the necessity of dismounting the optical elements and imaging device. Moreover, the position of the imaging device relative to the optical elements can be adjusted with the imaging unit kept hermetic.

BREIF DESCRIPTION OF THE DRAWINGS

BEST MODE FOR CARRYING OUT THE INVENTION

Figure 1:
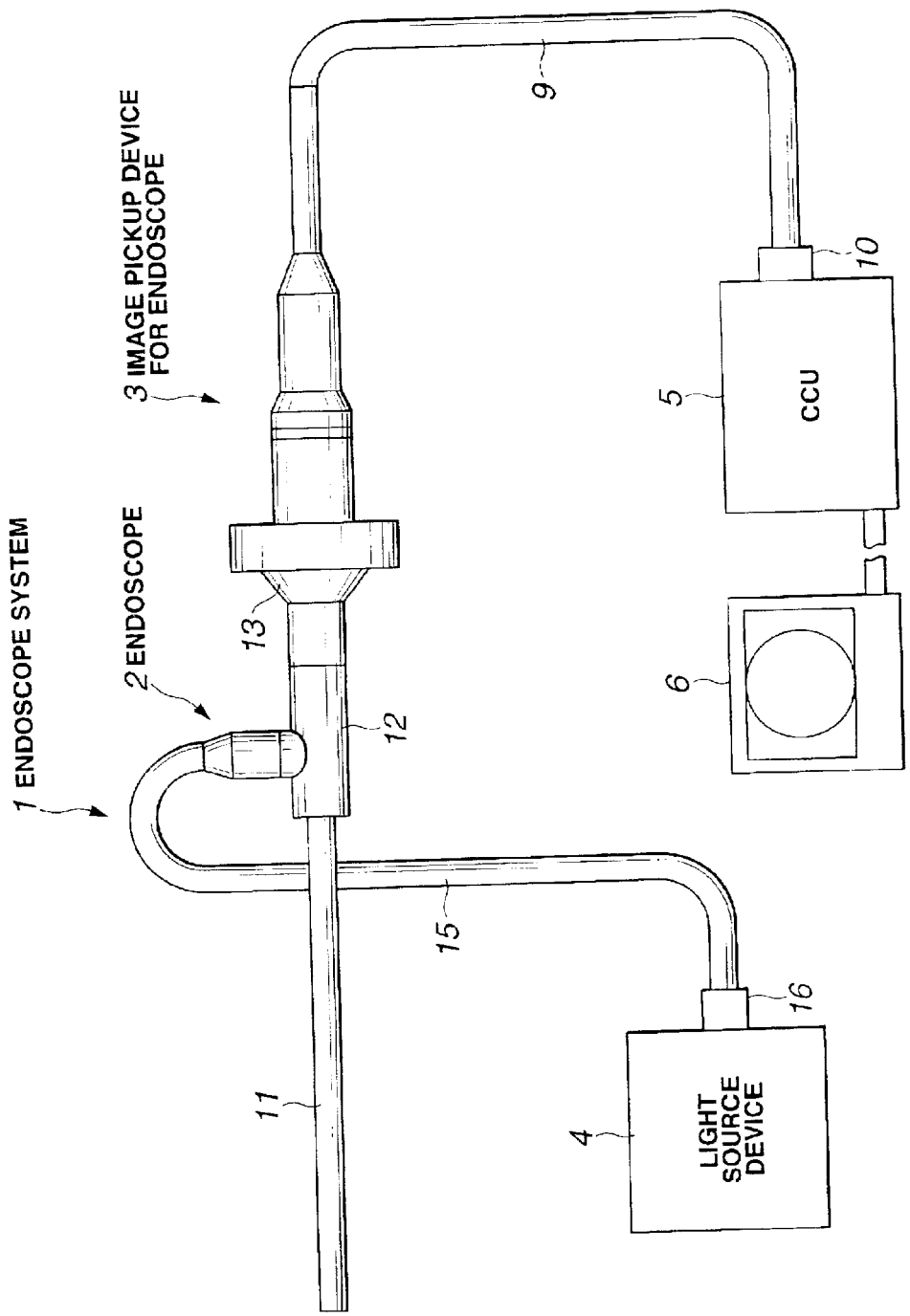
FIG. 1 is a perspective view for explaining the overall configuration of an endoscope system according to a first embodiment.

Referring to the drawings, embodiments of the present invention will be described below.

Figure 2:
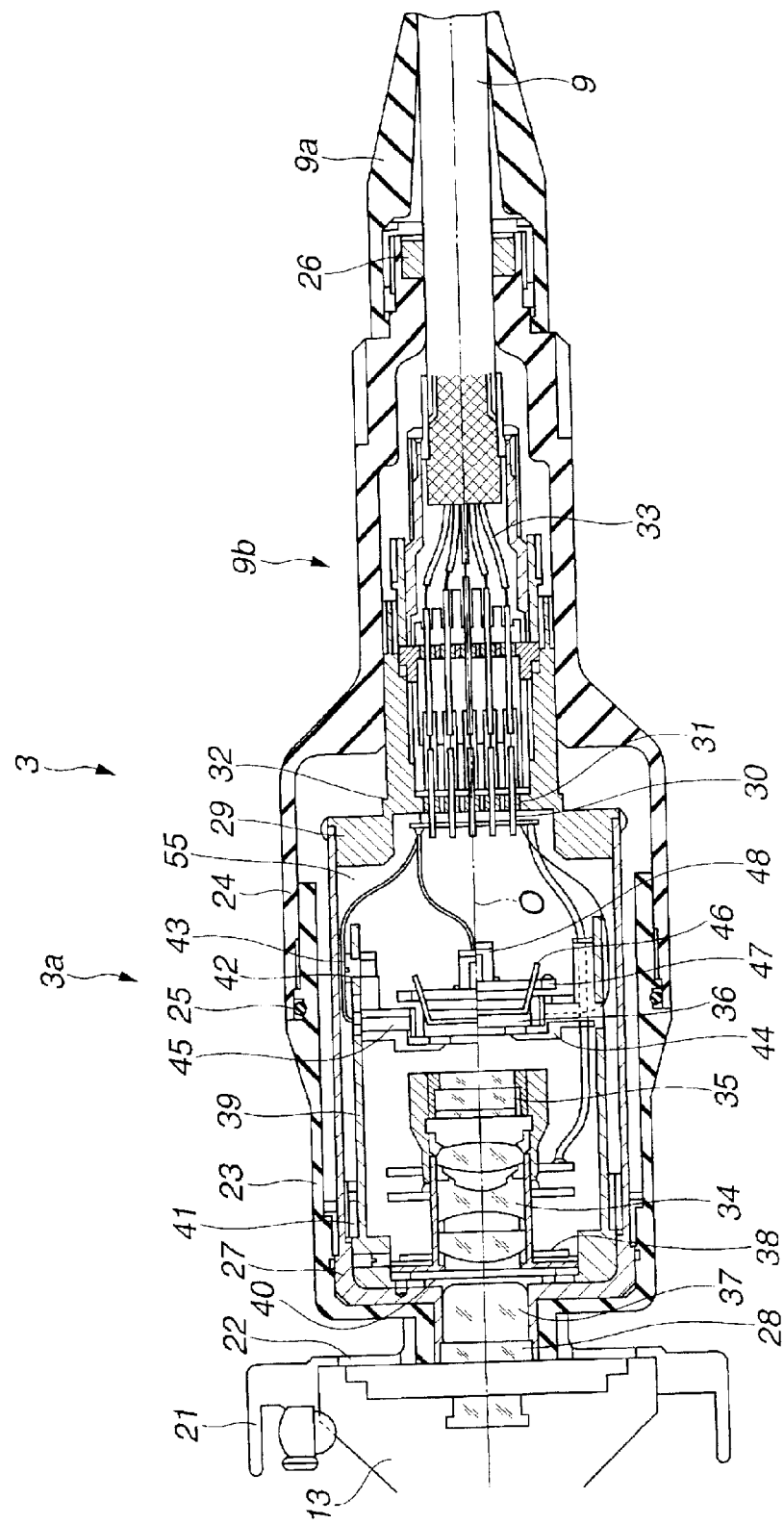
FIG. 2 is a sectional view for explaining an imaging unit for endoscopes (TV camera)
Figure 3:
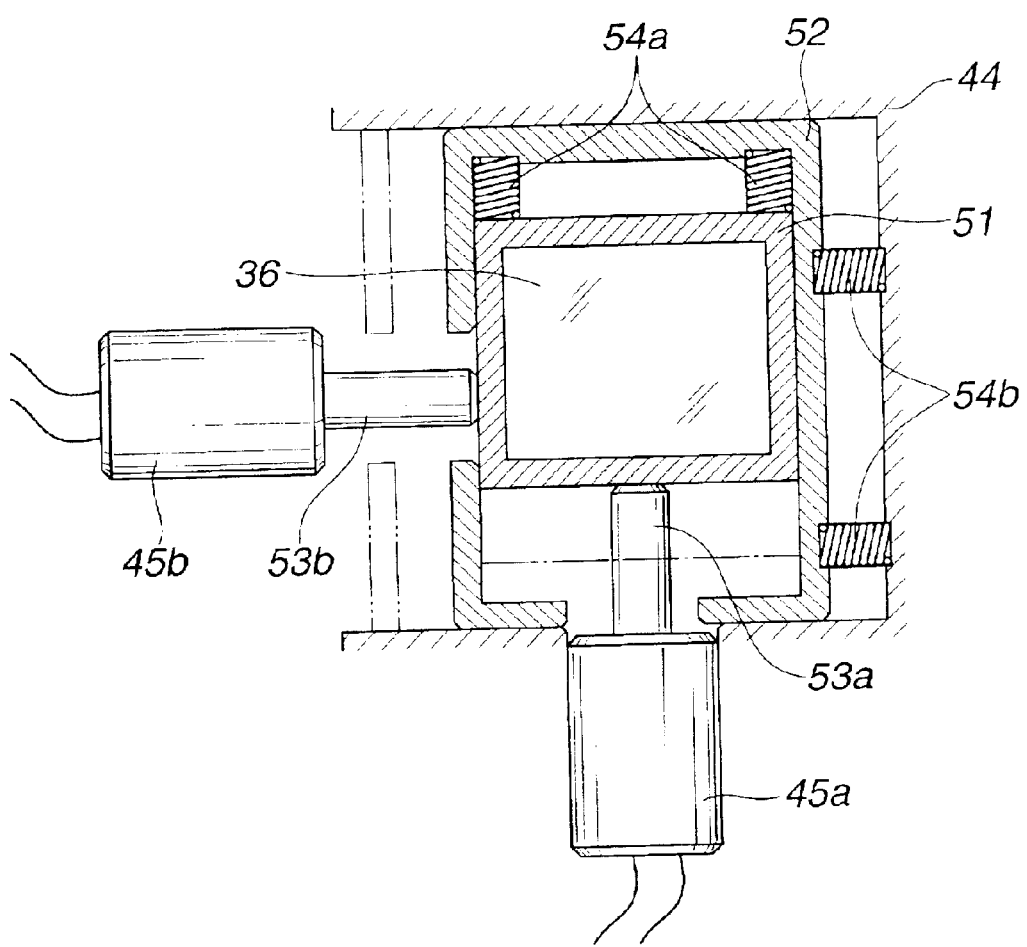
FIG. 3 is an explanatory diagram showing surroundings imaging device as a view seen from an endoscope.

FIG. 1 to FIG. 3 are concerned with a first embodiment of the present invention. FIG. 1 shows the overall configuration of an endoscope system that includes the first embodiment. FIG. 2 is a sectional view showing an imaging unit for endoscopes (TV camera) in accordance with the first embodiment for an explanatory purpose. FIG. 3 is an explanatory diagram showing an imaging device and its surroundings as a view seen from an endoscope. In FIG. 2, movable components are shown with the positions thereof differentiated between the upper and lower parts of the sectional view.

As shown in FIG. 1, an endoscope system 1 comprises an endoscope 2, a TV camera 3, a light source apparatus 4, a camera control unit (CCU) 5, and a monitor 6. The TV camera 3 is an imaging unit for endoscopes freely detachably attached to the endoscope 2. The light source apparatus 4 supplies illumination light to the endoscope 2. The CCU 5 processes a signal generated by the TV camera 3. The monitor 6 displays an image according to a video signal outputted from the CCU 5.

The endoscope 2 has an elongated insertion member 11, a large-diameter hand-held unit 12, an eyepiece unit 13, and a base. The hand-held unit 12 communicates with the rear end of the insertion member 11. The eyepiece unit 13 is formed at the rear end of the hand-held unit 12. The base is formed on the lateral surface of the hand-held unit 12. A light guide cable 15 is coupled to the base. A connector 16 attached to the end of the light guide cable 15 is joined to the light source apparatus 4 so that the connector 16 can be joined and disjoined freely.

When the connector 16 of the light guide cable 15 is joined to the light source apparatus 4, white light emanating from a lamp (not shown) in the light source apparatus 4 is emitted to the end surface of the light guide cable. Illumination light propagated over the light guide cable is supplied to a light guide that in the endoscope 2, and emitted forwards from an illumination window formed in the distal part of the insertion member 11. An object is thus illuminated.

An objective, which is not shown, incorporated in the distal part forms an image of the object illuminated with the illumination light emitted from the illumination window. The formed image is propagated to the eyepiece unit 13 side by means of a relay optical system, and viewed in enlargement through an eyepiece.

The TV camera 3 is freely detachably attached to the eyepiece unit 13. A solid-state imaging device (hereinafter, referred to as CCD) 36 is incorporated as an imaging means in the TV camera 3. The CCD 36 is connected to the CCU 5 through an attachable/detachable connector 10, which is fixed to the signal cable 9 extending from the TV camera 3, by way of the signal cable 9 (a signal line contained therein).

A CCD driving signal sent from a CCD driver (not shown) in the CCU 5 is transmitted over the signal cable 9, and applied to the CCD 36. With the application of the CCD driving signal, a signal photoelectrically converted by the CCD 36 is read and sent to a video signal generation circuit (not shown) in the CCU 5. The video signal generation circuit in turn generates a video signal, and an optical image is displayed on the display surface of the monitor 6 according to the video signal.

Next, the structure of the TV camera 3 that is an imaging unit for endoscopes referred to the present invention will be described concretely referred to FIG. 2.

The TV camera 3 comprises a camera head 3a and a cable 9b. The camera head 3a has the interior thereof hermetically sealed so that the camera head 3a can be autoclaved. The cable 9b is coupled to the rear end of the camera head 3a, and composed of an armor and a signal line that resist heat and steam. The cable 9b can therefore be autoclaved.

The camera head 3a is freely detachably attached to the eyepiece unit 13 of the endoscope 2 with a coupler 21 therebetween. The coupler 21 has a vent 22 through which the endoscope 2 is aerated, and is coupled to a first casing member 23. The first casing member 23 is joined to a second casing member 24 that is joined to the signal cable 9. An annular elastic member 25 is fitted in a space created between the first casing member 23 and the second casing member 24. An annular elastic member 26 is fitted in a space created between the second casing member 24 and the signal cable 9. Thus, the TV camera 3 is kept watertight.

A first hermetic frame 27 is abutted on the inner surface of the first casing member 23 in order to keep an optical window 28 hermetic. A second hermetic frame 29 is hermetically joined to the first hermetic frame 27. The first hermetic frame 27 is hermetically joined to the optical window 28 or second hermetic frame 29 by performing high-frequency soldering, laser welding, TIG welding, or resistance welding after the optical system to be described later and the imaging device are incorporated.

The TV camera 3 of the present embodiment is structured to enable adjustment of the position of the imaging device relative to the optical elements, which will be described later, while being kept hermetic. Specifically, a hermetic space 55 is created as a hermetic seal member by joining the first hermetic frame 27, optical window 28, second hermetic frame 29, and other members in order to prevent invasion of steam generated during autoclaving.

Contact pins 30 formed with metallic conductors have their peripheries joined by sintering a vitreous material 31, whereby a hermetic connector 32 is formed. The hermetic connector 32 is joined to the second hermetic frame 29. The signal cable 9 has lines 33 spliced to the hermetic connector 32, and is led to the CCU 5.

The CCD 36 is inserted into the first hermetic frame 27 through the coupler 21, and placed along the optical axis of optical elements with an image formation optical system 34 and a filter unit 35 placed between the coupler 21 and the CCD 36. The image formation optical system 34 and filter unit 35 correspond to the optical elements for forming an optical image propagated from the endoscope 2. A rod lens 37 offering an arbitrary refractive index is interposed between the optical window 28 and image formation optical system 34, whereby the length of an engaging member for engaging the coupler 21 with the first casing member 23 is increased, and a ventilation space on which the vent of the coupler 21 opens is expanded.

An aperture stop unit 38 having mechanical aperture blades that are driven with a motor is mounted on the outer circumference of the image formation optical system 34. The aperture stop unit 38 is secured with a screw so that an end surface 40 thereof will abut on an outer optical frame 39. The aperture stop unit 38 may be excluded supposing brightness or a depth of focus need not be adjusted.

The outer optical frame 39 is screwed to the first hermetic frame 27 using a ring 41, or may be fixed thereto through bonding. Moreover, the outer optical frame 39 has a focusing groove 42 formed therein along the optical axis. A device locking frame 44 has a focusing adjustment screw 43 engaged with the focusing groove 42 so that the position of the device locking frame 44 along the optical axis can be finely adjusted using the focusing adjustment screw 43 as a guide.

Actuators 45 movable in directions orthogonal to the optical axis are fixed to the device locking frame 44. Signal lines over which a driving signal is transmitted and which extend from the aperture stop unit 38 and actuators 45 are connected to a predetermined one of the contact pins 30 that juts in the second hermetic frame 29.

Leads 46 extending from the back of the CCD 36 are bundled and connected to a predetermined one of the contact pins 30, which juts in the second hermetic frame 29, via a substrate 47 and a connector 48.

Next, the components of a mechanism for adjusting the position of the CCD 36 will be described referring to FIG. 3.

A first movable device frame 51 serves as a package of the CCD 36. One of the vertical sides of the first movable device frame 51 or second movable device frame 52 and one of the lateral sides thereof are in contact with movable members 53a and 53b of actuators 45a and 45b. The actuators 45a and 45b move the first movable device frame 51 or second movable device frame 52 in directions perpendicular to the ones of the vertical sides and lateral sides of the first movable device frame 51 or second movable device frame 52. The first movable device frame 51 has two opposed sides thereof (left and right edges thereof in the figure) engaged with the second movable device frame 52 so that the first movable device frame 51 can slide freely. Elastic pieces 54a are sandwiched between the side of the first movable device frame 51, which is not in contact with the movable member 53a, and the second movable device frame 52.

The second movable device frame 52 is engaged with the inner wall of the device locking frame 44 so that the second movable device frame 42 can slide in the same direction as the direction in which the actuator 45b is movable. Elastic pieces 54b are sandwiched between the side of the second movable device frame 52, which is opposite to the side thereof that is in contact with the movable member 53b, and the device locking frame 44. The sides of the second movable device frame 52 in contact with the actuators 45 have escape holes bored therein for the movable members 53a and 53b. The diameters of the escape holes correspond to a distance by which the second movable device frame 52 moves. Escape holes for the movable members 53a and 53b are also bored in the device locking frame 44. The device locking frame 44 has the outer circumference thereof engaged with the outer optical frame 39.

The thus-structured mechanism for adjusting the position of the CCD 36 is used to assemble the TV camera 3.

The focusing adjustment screw 43 is loosened in order to move the device locking frame 44 and CCD 36 alike. The position of the CCD 36 relative to the image formation optical system 34 is previously adjusted in line with the focusing groove 42 that is formed in the outer optical frame 39 along the optical axis. Thereafter, the outer optical frame 39 is locked in the first hermetic frame 27, and the lines are connected. Thereafter, the first hermetic frame 27 and second hermetic frame 29 are joined hermetically and assembled.

The hermetic space 55 is created by joining the optical window 28, first hermetic frame 27, second hermetic frame 29, contact pins 30, and other members.

Thereafter, the other end of the signal cable 9 is inserted into the opening of the second casing member 24 that opens on the side of the endoscope. At this time, the second casing member 24 holds the annular elastic member 26. The signal cable 9 is then inserted into the opening of a sheath 9a that opens on the side of the endoscope. The sheath 9a protects the signal cable 9. The first hermetic frame 27 is inserted into the first casing member 23, which holds the annular elastic member 25, with the end of the first hermetic frame 27 headed for the optical window. The first hermetic frame 27 is inserted until the distal end thereof abuts on the first casing member 23. The periphery of the optical window 28 in the first hermetic frame 27 and the first casing member 23 are sealed with an adhesive if required. Thereafter, the second casing member 24 is mounted on the outer surface of the first casing member 23. The sheath 9a is pulled up to a predetermined position on the second casing member 24.

The TV camera 3 having the components assembled as mentioned above is attached firmly to the eyepiece unit 13 of the endoscope with the coupler 21 therebetween. Thereafter, the signal cable 9 is plugged in to the CCU 5. The endoscope 2 is now usable.

First, the light source apparatus 4 is connected to the endoscope 2 by way of the light guide cable 15. The CCU 5 and monitor 6 are then connected to the endoscope 2 and activated.

An object is illuminated by way of the light guide cable 15. The endoscope 2 is manipulated as already known in order to observe the object and pick up an optical image.

A view image provided by the endoscope 2 is passed through the optical window 28, image formation optical system 34, and filter unit 35 which are included in the imaging unit for endoscopes, via the eyepiece unit 13 of the endoscope, and propagated to the CCD 36. The filter unit 35 includes various optical filters. The CCD 36 converts the optical image of the object into an electric signal. The electric signal is transmitted to the CCU 5 over the signal cable 9. The CCU 5 converts the electric signal into a video signal that enables display of a picture. The monitor 6 displays a picture of the object.

The displayed position on the monitor 6 of a picture of an object may be deviated from a right position, a picture may lack any image, or an image may be eccentric. In this case, eccentricity is adjusted as mentioned above.

The focus of rays that carry an optical image passed through the eyepiece unit 13 of the endoscope is determined with the mechanical dimensions of relevant components. At the same time, the aperture blades included in the aperture stop unit 38 are driven based on a signal that represents the level of brightness and is sent from the CCD 36.

The actuators 45 are driven using an actuator control means (not shown), which is incorporated in or separated from the CCU 5 with respect to the center of an optical image passed through the eyepiece unit 13 of the endoscope. Herein, the center of the optical image is deviated from a right position. Thus, the CCD 36 is moved vertically or laterally to match with the optical image.

The TV camera 3 that is the imaging unit for endoscopes of the present embodiment can provide the advantages described below.

1) Eccentricity of an optical image propagated from the eyepiece unit 13 can be adjusted within a hermetically sealed space in which the relevant components will not be exposed to air. The eccentricity depends on an adopted endoscope that can be sterilized with high-pressure steam.

2) Eccentricity can be adjusted after the components of the TV camera 3 are assembled. A clearance can therefore be preserved between the image formation optical system 34 and outer optical frame 39, between the outer optical frame 39 and device locking frame 44, between the outer optical frame 39 and first hermetic frame 27. Moreover, dimensional precision does not count. This leads to an improved yield. Moreover, the aperture stop unit 38 that is a motor-driven aperture stop mechanism is incorporated in the TV camera 3. Therefore, once the distance between the image formation optical system 34 and CCD 36 is adjusted, a depth of focus can be improved using the aperture blades. This relieves a user of focusing.

3) If the rod lens 37 interposed between the optical window 28 and image formation optical system 34 offers a predetermined refractive index, a space can be created between the eyepiece unit 13 of the endoscope and the first casing member 23. The aperture stop unit can be located at an optimal position of an exit pupil, and locked readily and firmly. In addition, the efficiency in venting through the vent that opens between the endoscope 2 and TV camera 3 can be improved.

4) When the TV camera 3 is used in combination with an endoscope that is devoid of the aperture stop unit 38 and has the optical elements thereof adjusted in a predetermined manner, or an endoscope having a focusing mechanism, the TV camera 3 is usable without any problem. Besides, the TV camera 3 can be designed to be low-cost, compact, and lightweight.

Figure 4:
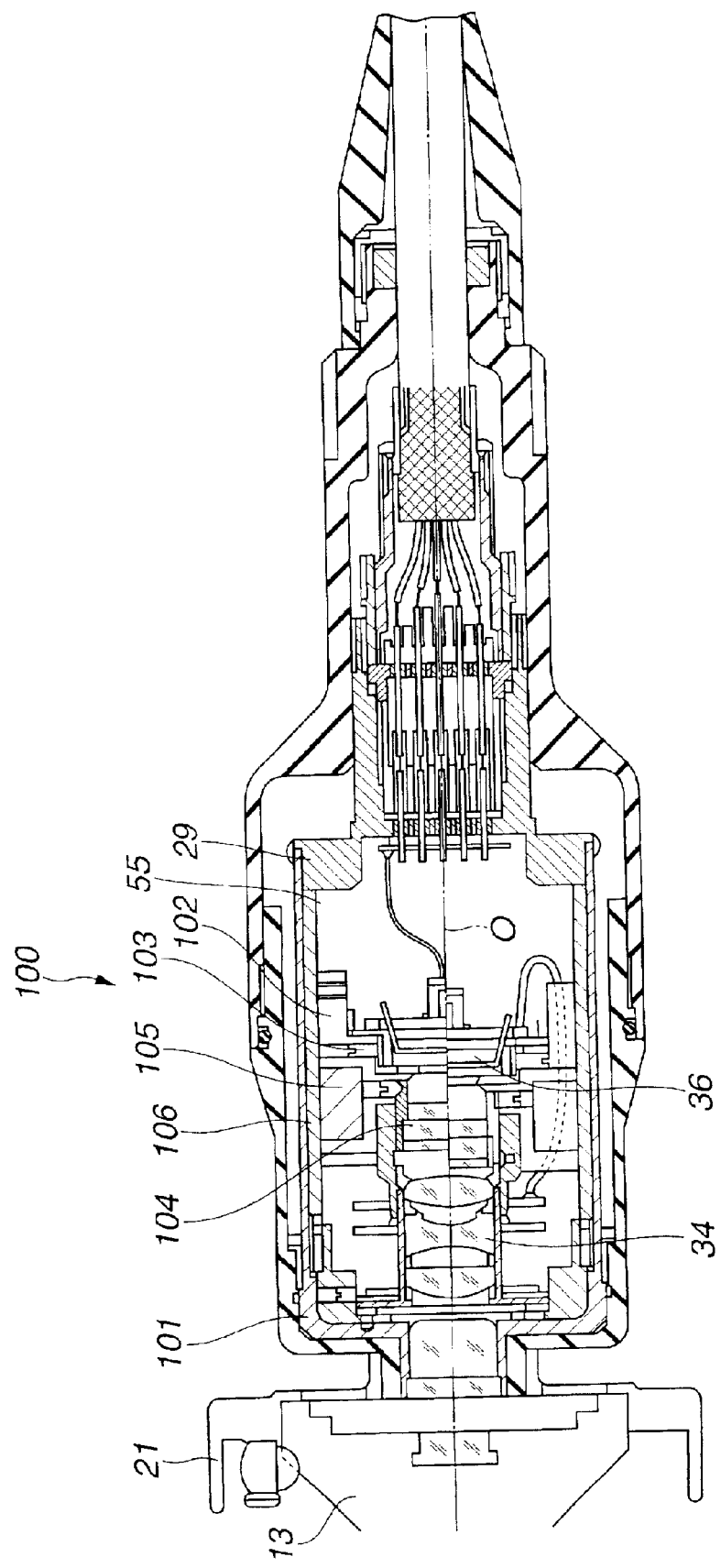
FIG. 4 is a sectional view for explaining an imaging unit for endoscopes (TV camera) according to a second embodiment.

FIG. 4 is a sectional view showing an imaging unit (TV camera) for endoscopes in accordance with a second embodiment of the present invention for an explanatory purpose. In FIG. 4, movable components are shown with the positions thereof differentiated between the upper and lower parts of the sectional view.

The TV camera 3 that is the imaging unit for endoscopes of the first embodiment has an eccentricity adjusting mechanism, which includes the actuators 45, as an imaging device driving means. The imaging unit for endoscopes of the present embodiment uses an eccentricity adjustment screw to adjust eccentricity, and has a focusing adjustment mechanism as the imaging device driving means. The other components are identical to those shown in FIG. 2. The description of the components will be omitted, and the same reference numerals will be assigned to the same components.

The CCD 36 is included in a hermetic frame 101 of a TV camera 100, which is the imaging unit for endoscopes, so that an optical image passed through the image formation optical system 34 will be converged on the CCD 36. The CCD 36 is enclosed in a movable frame 102 that includes a predetermined eccentricity adjusting mechanism. The positions of the four sides of the CCD 36 are adjusted using an eccentricity adjustment screw 103 screwed to the movable frame 102 so that the CCD 36 will be located at a predetermined position, or basically, the center of the CCD 36 will be dimensionally aligned with the center of an optical image propagated from the eyepiece unit 13.

A filter unit 104 including an infrared cut filter is located in front of the movable frame 102. A driver 105 is located near the outer edge of the movable frame 102, and is movable along the optical axis of the image formation optical system 34 relative to a stationary member 106 fixed to the inner surface of the hermetic frame 101.

A driving signal generated by the driver 105 is transmitted over a driver signal line connected to a predetermined one of the contact pins 30 that juts in the second hermetic frame 29. The driver 105 is thus electrically connected to a control circuit (not shown) incorporated in or separated from the CCU 5. The signal is transferred to the control circuit through a switch located at any position (not shown).

After the TV camera 100 has the foregoing components thereof assembled, the imaging unit for endoscopes is attached to the eyepiece unit 13 of the endoscope with the coupler 21 therebetween. The endoscope 2 is now usable.

A view image picked up by the endoscope 2 is passed through the optical window 28, image formation optical system 34, and filter unit 104, which are incorporated in the imaging unit for endoscopes, via the eyepiece unit 13 of the endoscope, and propagated to the CCD 36. The filter unit 104 includes various optical filters.

Next, the TV camera 100 is focused.

The driver 105 is moved in an optical-axis direction relative to the stationary member 106 according to an electric signal that is generated by via the control circuit and transferred through a switch (not shown). The movable frame 102 and CCD 36 lying in the hermetic space 55 are moved in the optical-axis direction for the purpose of adjusting the position of the CCD 36.

The TV camera 100 that is the imaging unit for endoscopes of the present embodiment provides the advantages described below.

1) Even if an observation optical system incorporated in an endoscope has not been focused (for example, when an endoscope manufactured by a different manufacturer is employed), focusing can be arbitrarily achieved within the hermetic space 55.

2) Even when an optical image is so dark that the aperture stop unit 38 does not move (the aperture stop unit 38 does not work), any focus can be obtained.

3) If an image formation lens included in the aperture stop unit 38 having a rotating mechanism must be moved, the unit itself must be made larger in size or the (effective) diameter of the lens must be made smaller. However, this is advantageous in terms of the design and shape of a mechanism for moving the CCD 36.

4) The center of the CCD 36 can be substantially aligned with the center of an optical image (an ideal position) propagated from the eyepiece unit 13 of the endoscope by performing adjustment in the course of assembling.

5) Even when the aperture stop unit 38 that is useful in improving a depth of focus is excluded, focusing can be achieved arbitrarily. Therefore, the TV camera will never be unusable because it is out of focus. This results in the reduced costs of the TV camera.

Figure 5:
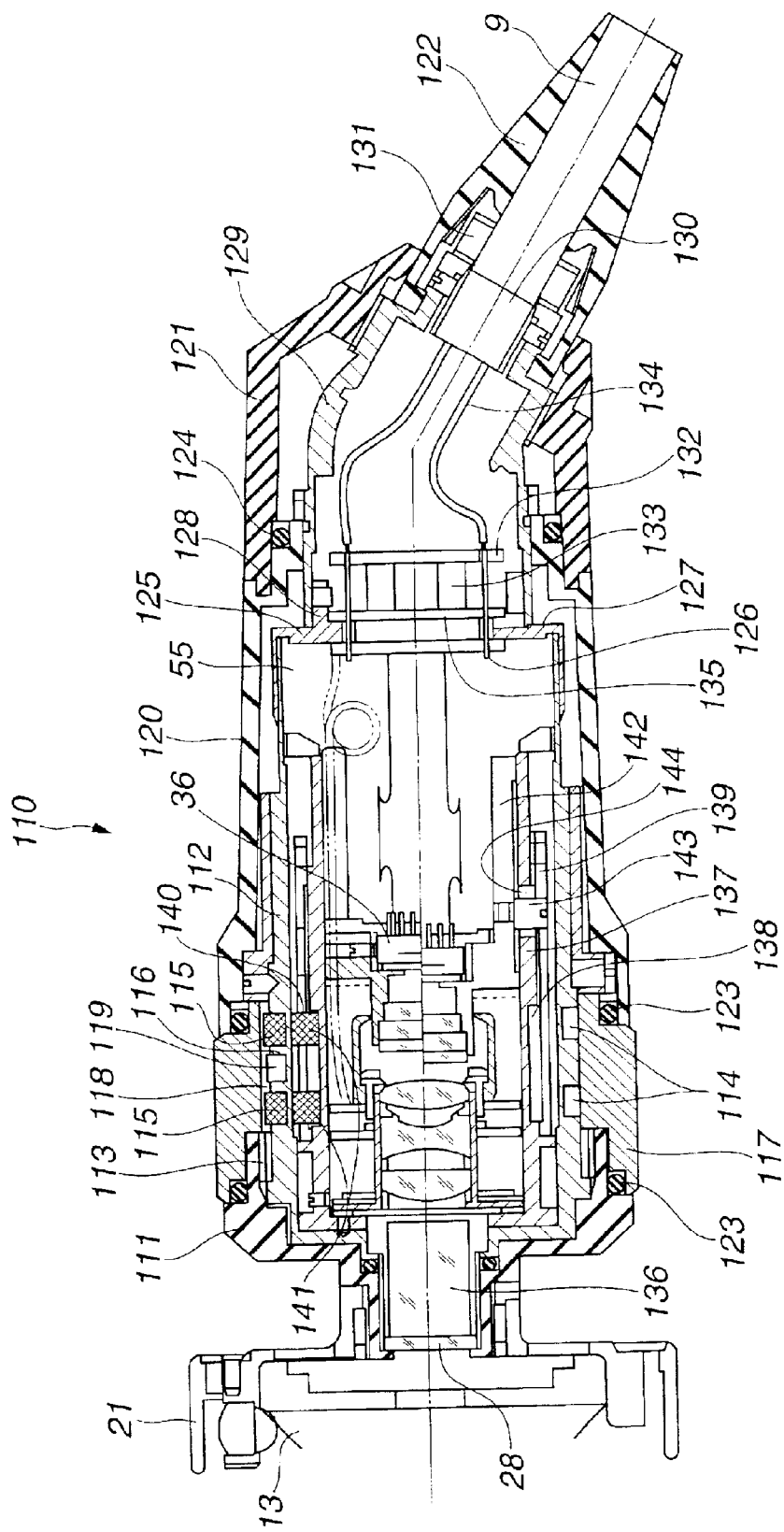
FIG. 5 is a sectional view for explaining an imaging unit for endoscopes (TV camera) according to a third embodiment.

FIG. 5 is a sectional view showing an imaging unit for endoscopes (TV camera) of the third embodiment of the present invention. In FIG. 5, movable components are shown with the positions thereof differentiated between the upper and lower parts of the sectional view.

In the imaging units for endoscopes of the first and second embodiments, the actuators 45 or driver 105 is adopted as an imaging device driving means and controlled using an electric signal. In the imaging unit for endoscopes of the present embodiment, a mechanism including magnets and enabling manual focusing is adopted as the imaging device driving means. The other components are identical to those shown in FIG. 2. The description of the components will be omitted and the same reference numerals will be assigned to the same components.

A hermetic frame 112 is screwed to a casing member 111 of a TV camera 110, which is the imaging unit for endoscopes of the present embodiment, by meshing screws 113. The hermetic frame 112 is made of a nonmagnetic material for fear the hermetic frame 112 may affect magnetic force that works on the driver 105. The coupler 21 is fixed to the casing member 111. A magnet groove 114 is formed in the periphery of the hermetic frame 112 throughout the periphery or by a predetermined length. At least one magnet 115 is put in the magnet groove 114. Similarly to the magnet groove 114, a rotation restriction groove 116 of a predetermined length is formed in the outer circumference of the hermetic frame 112 separately from the magnet groove 114.

A focus ring 117 covering the magnet 115 is mounted on the outer surface of the hermetic frame 112. A stopper engagement groove 118 is formed in the inner surface of the focus ring 117, and extended along the optical axis of an optical system incorporated in the TV camera. A stopper 119 is put in the rotation restriction groove 116 while being fitted in the stopper engagement groove 118. The focus ring 117 communicates with a casing member 120, a casing member 121, and an anti-breakage member 122 that protects the signal cable 9. The casing member 111 and focus ring 117 or the casing member 120 and focus ring 117 are joined to each other in a watertight manner using an annular elastic member 123. The casing member 120 and casing member 121 are also joined with each other in a watertight manner using an annular elastic member 124.

An open end of the hermetic frame 112 that opens onto the signal cable 9 side is hermetically joined to a hermetic frame 125. Hermetic contacts are formed in the center of the hermetic frame 125 with the peripheries of contact pins 126 sealed by sintering a vitreous material. Moreover, a projection 128 is projected along the optical axis from the end of the hermetic frame 125 that opens onto the signal cable 9 so that the projection 128 will encircle the contact pins 126. The end of the hermetic frame 125 having the projection 128 is joined to a shield frame 129.

The end of the hermetic frame 125 is joined to the shield frame 129 with electric continuity retained. The shield frame 129 is electrically coupled to a folded part of a general shield 130 attached to the end of the signal cable 9. The signal cable 9 and shield frame 129 and the shield frame 129 and casing member 121 are joined to each other in a watertight manner using an annular elastic member 131 and the anti-breakage member 122 respectively.

At the end of the hermetic frame 125 that opens onto the signal cable 9, a substrate 132 is fixed to the contact pins 126 by soldering. An SMD-type connector 133 is placed on the substrate 132. The hermetic frame 125 is connected to harnesses 134, which extend from the signal cable 9, with a substrate 135 and the connector 133 therebetween.

The optical window 28 is hermetically joined to the end of the hermetic frame 112 that opens onto the coupler 21 side. A rod lens 136 is placed inside the optical window 28. The aperture stop unit 38 is placed so that the aperture blades will be located near the end of the rod lens 136 on the side of the signal cable 9. The image formation optical system 34 is incorporated inside the aperture stop unit 38, and enclosed in an outer optical frame 137 engaged with the hermetic frame 112, and locked in the outer optical frame 137 in the optical-axis directions and circumferential directions alike.

A magnet receptor groove 138 is formed in the periphery of the outer optical frame 137 at a position at which the magnet receptor groove 138 coincides with the magnet 115 embedded in the hermetic frame 112. The magnet receptor groove 138 extends in a circumferential direction in the periphery of the outer optical frame 137. A cam ring 139 is interposed between the hermetic frame 112 and outer optical frame 137 so that the cam ring 139 can rotate in circumferential directions on the periphery of the hermetic frame 112. A magnet positioning hole 140 is formed in the cam ring 139 at a position at which the magnet positioning hole 140 will be aligned with the magnet 115. A magnet 141 is fitted in the magnet positioning hole 140, whereby the pair of magnets 115 and 141 constructs a closed magnetic circuit.

The cam ring 139 has a cam groove, which has a predetermined lead angle, formed near the CCD 36 to extend along the optical axis. A cam pin 143 fixed to an imaging device frame 142 is engaged with the cam groove. The cam pin 143 is also engaged with a rectilinear groove 144 that is formed in the periphery of the outer optical fame 137 to extend along the optical axis.

After the TV camera 110 has the foregoing components thereof assembled, the TV camera 110 is attached to the eyepiece unit 13 of the endoscope with the coupler 21 therebetween. The endoscope 2 is now usable.

A view image picked up by the endoscope 2 is passed through the optical window 28, image formation optical system 34, and filter unit 35, which are incorporated in the imaging unit for endoscopes, via the eyepiece unit 13 of the endoscope, and propagated to the CCD 36. The filter unit 35 includes various optical filters. The focus of rays carrying an optical image propagated from the eyepiece unit 13 of the endoscope is generally determined with the mechanical dimensions of relevant components. The focus thereof is finely adjusted by driving the aperture blades of the aperture stop unit 38 according to a signal that represents brightness and is sent from the CCD 36.

Next, the TV camera 110 is focused.

When the focus ring 117 is turned, the stopper 119 and magnet 115 rotate until the stopper 119 is fitted into the rotation restriction groove 116. The magnet 141 that constructs a closed magnetic circuit in cooperation with the magnet 115 rotates along with the movement of the magnet 115 due to magnetic force. At this time, the cam ring 139 rotates. This causes the cam pin 143 engaged with the rectilinear groove 144 to move along the rectilinear groove 144 in an optical-axis direction. Consequently, the positions along the optical axis of the imaging device frame 142 and CCD 36 lying in the hermetic space 55 defined with the hermetic frame 112 and hermetic frame 125 can be adjusted without being rotated about the optical axis.

The foregoing TV camera 110 that is the imaging unit for endoscopes of the present embodiment can provide the advantages described below.

1) Since an electric signal need not be transmitted to a means for moving the CCD 36, a control circuit for transferring a signal to the camera control unit (CCU) 5 is unnecessary. This results in reduction in costs.

2) Unlike the employment of the actuators 45 in the first embodiment, precision does not count. Therefore, assembling is achieved readily.

3) Even if a clearance is widened in order to reduce frictional resistance derived from sliding, eccentricity of the CCD 36 can be adjusted in advance. The eccentricity of the CCD 36 can therefore be confined to a desired degree.

A TV camera that is an imaging unit for endoscopes of the present embodiment is a combination of the TV cameras of the first to third embodiments. For example, as an imaging device driving means, both the eccentricity adjusting mechanism including the actuators 45 and the focusing mechanism including the driver 105 may be included. Otherwise, both the eccentricity adjusting mechanism including the actuators 45 and the focusing mechanism enabling manual focusing using the magnet 115 may be included. The other components are identical to those shown in FIG. 2 to FIG. 5. The description of the components and the operations of the present embodiment will be omitted.

The imaging unit for endoscopes of the present embodiment provides the same advantages as the imaging units for endoscopes of the first to third embodiments. In addition, after the components of the imaging unit are assembled, a user can arbitrarily adjust the eccentricity of an imaging device or focus the imaging device.

Figure 6:
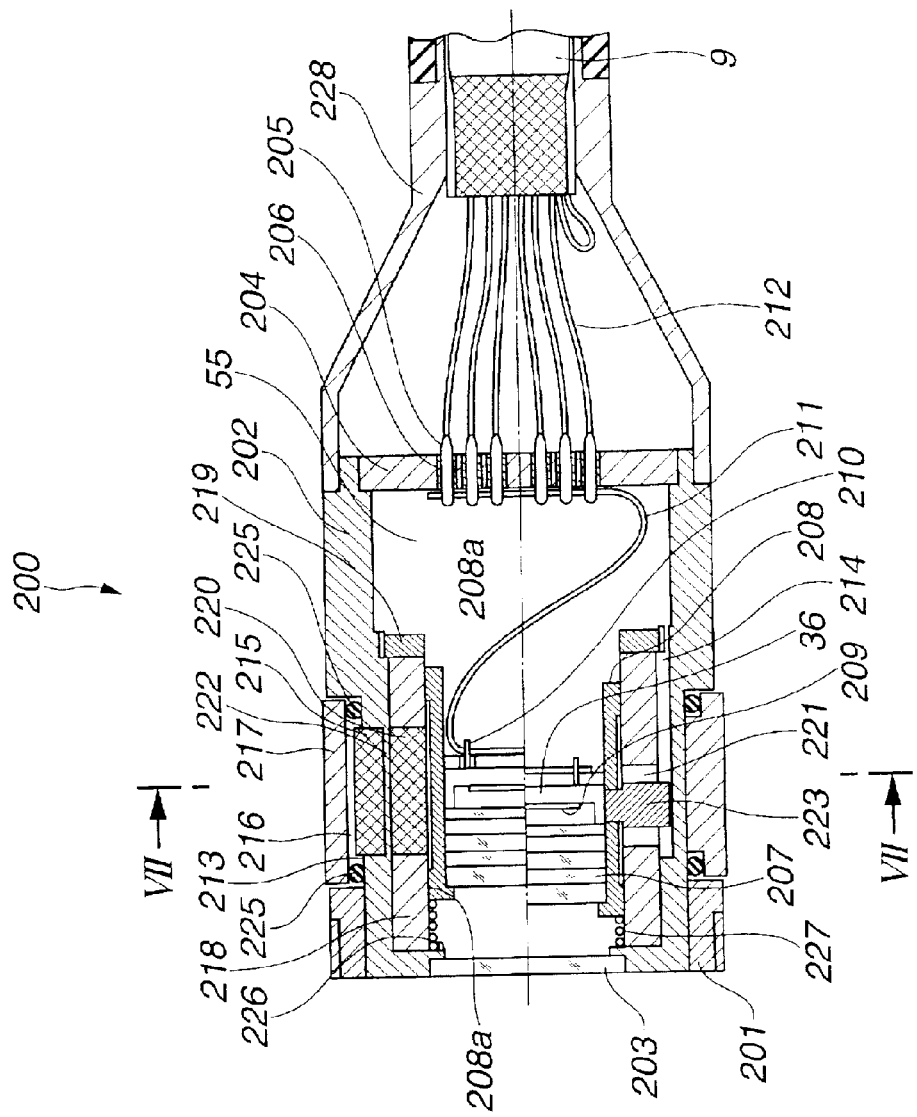
FIG. 6 is a sectional view of a camera head that does not hold an image formation optical system but incorporates a CCD therein according to a fifth embodiment.
Figure 7:
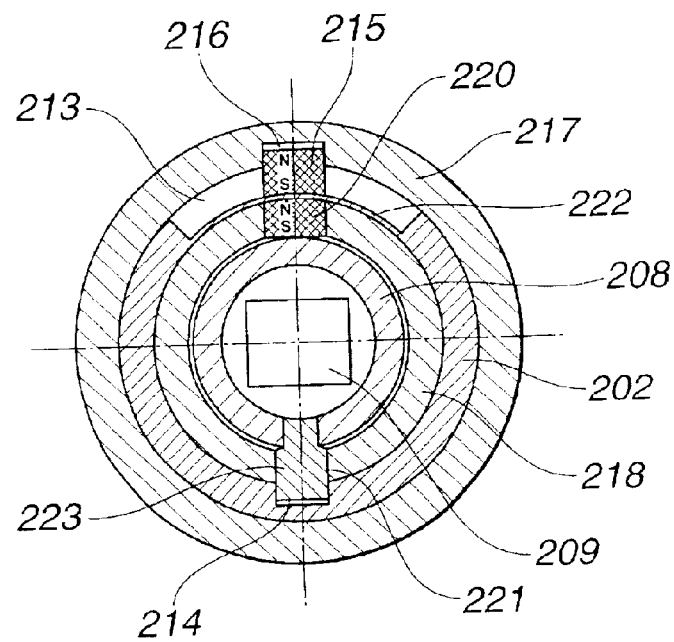
FIG. 7 is a VII—VII sectional view of the camera head shown in FIG. 6.

FIG. 6 and FIG. 7 are concerned with the fifth embodiment. FIG. 6 is a sectional view of a camera head devoid of an image formation optical system and with a built-in CCD. FIG. 7 is a VII—VII sectional view of the camera head shown in FIG. 6. In FIG. 6, movable components are shown with the positions thereof differentiated between the upper and lower parts of the sectional view.

A TV camera that is an imaging unit for endoscopes of the present embodiment has an optical adaptor (not shown) separated from a camera head 200 in which the CCD 36 that is an imaging device is incorporated. The optical adaptor has an image formation optical system incorporated therein, and is attached to the eyepiece unit 13 of the endoscope (see FIG. 2). An imaging surface 209 of the CCD 36 is located nearly in the middle of an engagement length of an imaging device frame 208 that can move along the optical axis of an optical system including the CCD while holding the CCD 36. A user can externally adjust the position of the optical system using the focusing mechanism or the like without the necessity of touching the optical systems.

The camera head 200 and optical adaptor (not shown) are screwed to each other with a camera mount 201 attached to the face of the camera head 200 therebetween. The ray axis of an optical image propagated from the eyepiece unit 13 of the endoscope (see FIG. 2) is aligned with the optical axes of the optical adaptor and camera head 200.

The mount 201 is fixed to the outer circumference of the front end of a hermetic frame 202 made of a nonmagnetic material. An optical window 203 made of a heat-resisting optical material such as sapphire is joined to the front end of the hermetic frame 202, which opens onto the endoscope, with the hermetic frame 202 kept hermetic.

A hermetic connector 204 is joined to the rear end of the hermetic frame 202 with the hermetic frame 202 kept hermetic. A plurality of contact pins 205 that are conductors is embedded in the hermetic connector 204. Herein, since a vitreous material 206 applied to the peripheries of the contact pins 205 is sintered, the hermetic frame 202 is kept hermetic and the contact pins 205 are isolated from one another.

The hermetic frame 202 is cylindrical, and sealed hermetically with the optical window 203 and hermetic connector 204 joined to the front and rear ends thereof. The hermetic space 55 is therefore created within the hermetic frame 202.

A guide groove 213 having a predetermined width is formed in the outer face of the hermetic frame 202 in a circumferential direction. The guide groove 213 will not penetrate through the hermetic frame 202. A rectangular magnet 215 that is polarized in a radial direction is put in the guide groove 213 so that it can freely move along the guide groove 213.

An outer ring 217 used to focus the TV camera is mounted on the outer circumference of the hermetic frame 202 while being permitted to move in circumferential directions. The top of the magnet 215 jutted out of the guide groove 213 is fitted in a concave linear key groove 216 formed in the inner surface of the outer ring 217 along the optical axis. When the outer ring 217 is turned, the magnet 215 rotates along the guide groove 213 responsively to the turn of the outer ring 217 in the same direction as a direction in which the outer ring 217 is turned.

An annular elastic member 225 is interposed between the hermetic frame 202 and outer ring 217 in order to keep the hermetic frame 202 watertight and produce appropriate torque that permits the outer ring 217 to rotate.

An inner ring 218 is placed inside the inner surface of the hermetic frame 202 so that the inner ring 218 can slide freely on the inner surface of the hermetic frame 202. The movement of the inner ring 218 in an optical-axis direction is restricted by a front end 226 of the hermetic frame 202 and a presser ring 219 fixed to the rear end of the inner ring 218. The distance between the front end 226 and presser ring 219 is slightly larger than the width of the inner ring 218. The inner ring 218 is therefore held inside the inner surface of the hermetic frame 202 while being permitted to rotate.

A magnet 220 having the same shape as the magnet 215 is embedded in the inner ring 218, and opposed to the magnet 215 with a thin part 222 of the hermetic frame 202 therebetween.

A helical cam groove 221 is formed in the inner ring 218 at a position at which the cam groove 221 does not interfere with the magnet 220 (in the figure, a position at which the cam groove 221 is opposed to the magnet 220 with the center of the hermetic frame along the optical axis therebetween). A cam pin 223 is passed through the cam groove 221. The bottom of the cam pin 223 is fitted in a rectilinear groove 214, which is formed in the inner surface of the hermetic frame 202 not to penetrate through the hermetic frame 202. The rectilinear groove 214 is formed along the optical axis, permits the cam pin 223 to move in optical-axis directions, and restricts the movement of the cam pin 223 in circumferential directions.

The magnets 215 and 220 constitute a closed magnetic circuit with the thin part 222 therebetween, and are magnetically coupled to each other.

The imaging device frame 208 is placed inside the inner ring 218. Sliding surfaces 208a are formed as the surfaces of the front and rear parts of the imaging device frame 208. The sliding surfaces 208a are in contact with the inner surface of the inner ring 218 so that the imaging device frame 208 can slide on the inner surface of the inner ring 218. The periphery of an intermediate part between the front and rear parts having the sliding surfaces 208a is not in contact with the inner ring 218 but opposed to the inner ring 208. The distance between the front and rear parts having the sliding surfaces 208a shall be referred to as an engagement length.

The tip of the cam pin 223 jutted out of the cam groove 221 is fitted in the imaging device frame 208. Therefore, when the inner ring 218 is turned, the cam pin 223 inserted in the cam groove 221 is pressured to move in an optical-axis direction along the rectilinear groove 214 formed in the inner surface of the hermetic frame 202. Consequently, the imaging device frame 208 that locks the tip of the cam pin 223 is advanced or withdrawn in the optical-axis direction.

A filter unit 207 including an infrared cut filter and the CCD 36 are held in the imaging device frame 208 in that order from the front end thereof. The imaging surface 209 of the CCD 36 is located nearly in the middle of the engagement length of the imaging device frame 208.

The CCD 36 has contacts 210 thereof electrically connected to the hermetic connector 204 by way of a flexible substrate 211, and further connected to the signal cable 9 by way of harnesses 212.

In this case, a compression coil spring 227 is, as shown in FIG. 6, interposed between the front end of the imaging device frame 208 and the front end 226 of the hermetic frame 202, whereby the imaging device frame 208 is constrained to move in one optical-axis direction all the time. The backlash of the imaging device frame 208 is thus minimized.

A rear cover 228 is hermetically joined to the end of the hermetic frame 202 on the side of the signal cable 9 side and to the signal cable 9 side. Thus, the rear cover 228 covers the signal cable 9 and harnesses 212.

The thus-structured camera head 200 is attached to the optical adaptor that is not shown in order to construct the TV camera that is the imaging unit for endoscopes. Thereafter, the TV camera is attached to the eyepiece unit 13 of the endoscope. When the endoscope is used, the TV camera is focused.

When the outer ring 217 is turned, the magnet 215 communicating with the inner surface of the outer ring 217 is rotated along the guide groove 213, which is formed in the outer circumference of the hermetic frame 202, in the same direction as a direction in which the outer ring 217 is turned.

At this time, the magnet 220 magnetically coupled to the magnet 215 with the thin part 222 of the hermetic frame 202 therebetween follows the magnet 215 to move in the same direction as the direction in which the magnet 215 is rotated. Since the magnet 220 is embedded in the inner ring 218, the turn of the outer ring 217 causes the inner ring 218 to rotate.

When the inner ring 218 rotates, the cam pin 223 piercing through the cam groove 221 formed in the inner ring 218 is pressured. The bottom of the cam pin 223 is fitted in the rectilinear groove 214 that is formed in the inner surface of the hermetic frame 202 and extended along the optical axis. The rotation of the cam pin 223 is therefore restricted. Consequently, the cam pin 223 moves in an optical-axis direction with the rotation of the inner ring 218.

Consequently, the imaging device frame 208 fixed to the top of the cam pin 223 advances or withdraws in the optical-axis direction. Thus, the CCD 36 that is housed in the hermetic space 55 of the hermetic frame 202 is externally advanced or withdrawn while being untouched by a user, whereby the TV camera can be focused on an optical image.

When the imaging device frame 208 is moved in an optical-axis direction by means of the cam pin 223, the cam pin 223 is pressured within the cam groove 221. When the imaging device frame 208 slides on the inner surface of the inner ring 218, little frictional force is generated. The imaging device frame 208 is likely to slightly tilt (swing) with respect to the optical axis because of a backlash created between the inner surface of the inner ring 218 and the sliding surfaces 208a of the front and rear parts of the imaging device frame 208.

In this case, according to the present embodiment, the imaging device frame 208 has only the sliding surfaces 208a of the front and rear end parts thereof kept in contact with the inner surface of the inner ring 218. Minimum frictional force therefore results from sliding. Moreover, the imaging surface 209 of the CCD 36 is located nearly in the middle of the engagement length, or in other words, with the center thereof aligned with the intersection between a line segment, which is perpendicular to the optical axis and passes through the middle of the engagement length, and the optical axis. The portion of the imaging device frame 208 in the middle of the engagement length makes the smallest displacement (backlash).

As mentioned above, the TV camera that is the imaging unit for endoscopes of the present embodiment can provide the advantages described below.

1) Since the TV camera that is the imaging unit for endoscopes consists mainly of the camera head 200 and optical adaptor that are separated apparatuses, the TV camera can be used in combination of any image formation optical system (an optical system that offers any power, that has a zoom lens of any power, or that includes or does not include an aperture stop unit).

2) Since the hermetic space is narrow, satisfactory resistance to a change in pressure (environmental change) can be ensured.

3) Since magnets are placed away from the aperture stop unit 38, influence of magnetic force on a mechanism for driving the aperture stop unit 38 need not be concerned about.

4) Even if the imaging device frame 208 swings, since the imaging surface 209 of the CCD 36 is located on or near a plane that passes the middle of the engagement length at which the imaging device frame 208 makes the smallest displacement, influence of eccentricity derived from the swing can be minimized.

Figure 8:
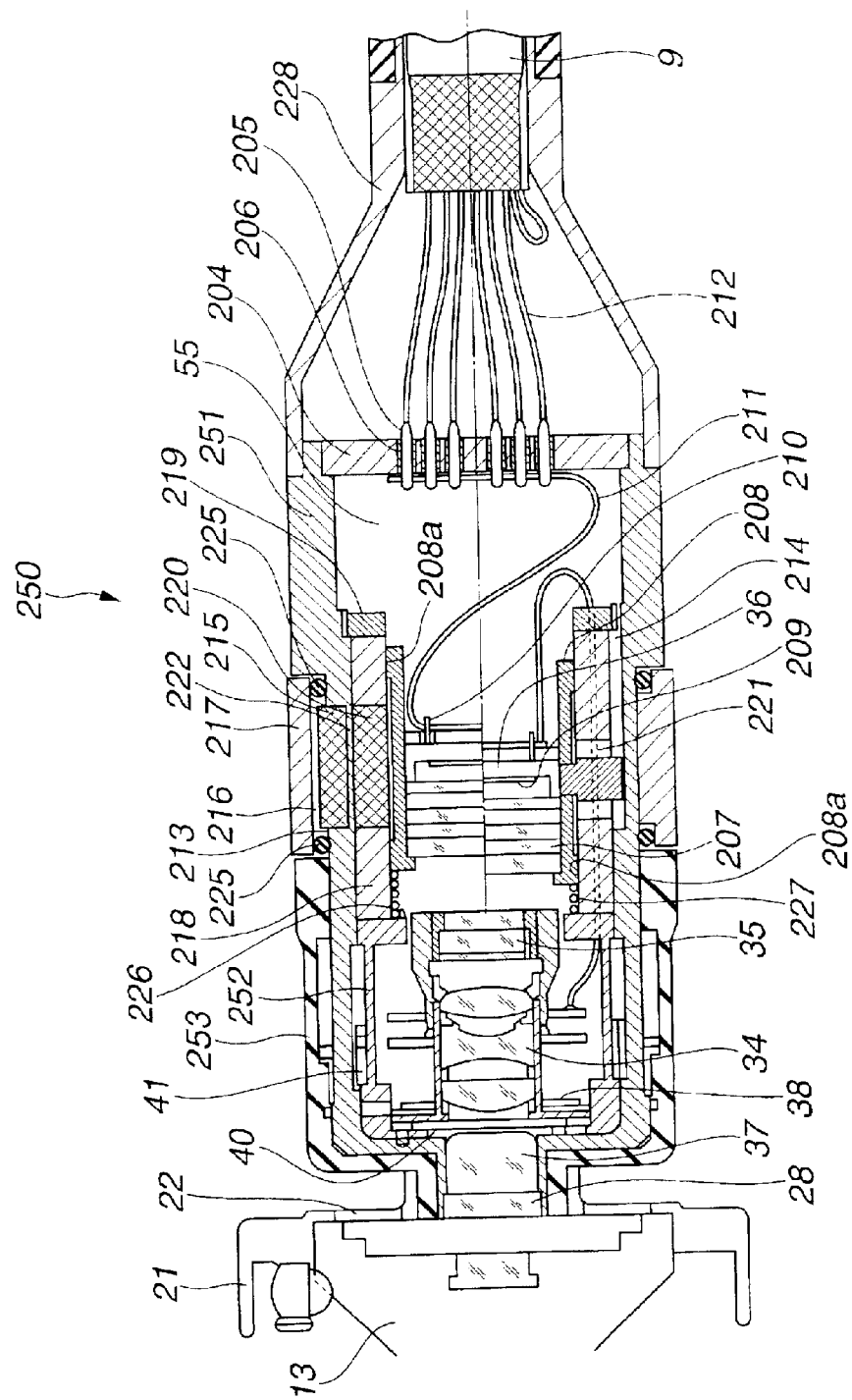
FIG. 8 is a sectional view showing the structure of an imaging unit for endoscopes (TV camera) according to a sixth embodiment.

FIG. 8 is a sectional view explaining an imaging unit for endoscopes (TV camera) of a sixth embodiment of the present invention for an explanatory purpose. In FIG. 8, movable components are shown with the positions thereof differentiated between the upper and lower parts of the sectional view. The same reference numerals will be assigned to components identical to those shown in FIG. 2 or FIG. 6, and the description of the components will be omitted.

In the imaging unit for endoscopes (TV camera) of the first embodiment, the eccentricity adjusting mechanism is adopted as the imaging device driving means. The CCD 36 enclosed in the hermetic frame is moved in a direction orthogonal to the optical axis of the image formation optical system within a hermetically sealed space. Eccentricity of the CCD 36 relative to an optical image is thus adjusted. In the imaging unit for endoscopes of the present embodiment, the focusing mechanism described in relation to the fifth embodiment is used to move the CCD 36 in optical-axis directions.

In a TV camera 250 that is an imaging unit for endoscopes of the present embodiment, the image formation optical system 34 is incorporated in a portion of a hermetic frame 251 located on the side of the eyepiece unit 13 of the endoscope. The rear end of an outer optical frame 252 that encircles the outer circumference of the image formation optical system 34 serves as the front end 226. The inner ring 218 is sandwiched between the front end 226 and a presser ring 219 fixed to the inner surface of the hermetic frame 251 while being permitted to solely rotate. The compression coil spring 227 is interposed between the front end of the imaging device frame 208, which holds the CCD 36, and the front end 226 that is the rear end of the outer optical frame 252. The imaging device frame 208 slides in contact with the inner surface of the inner ring 218. The compression coil spring 227 always constrains the imaging device frame 208 to move in one optical-axis direction.

A casing member 253 that locks the coupler 21 is mounted on the outer circumference of the front part of the hermetic frame 251. The outer ring 217 used to focus the TV camera is interposed between the rear end of the casing member 253 and the step of the hermetic frame 251 while being permitted to move in circumferential directions.

Operations to be made for focusing responsively to the turn of the outer ring 217 of the TV camera 250 are identical to those made in the fifth embodiment. The description of the movements will be omitted.

The present embodiment provides the same advantages as the fifth embodiment. In addition, the present embodiment can provide the advantages described below.

1) A turning pair need not be formed in the imaging device frame 208 and in the inner ring 218. The imaging device frame 208 and inner ring 218 can therefore be machined readily. Moreover, no special adjustment need be performed in order to adjust eccentricity of a monitor image by a desired degree or adjust the swing of the imaging device frame by a desired degree.

2) Since a turning pair need not be formed in the imaging device frame 208 and in the inner ring 218, the dimension in a radial direction of the TV camera can be made shorter for the dimension thereof along the optical axis thereof.

3) An operator can focus the hermetic frame 251 irrespective of whether the swing of the imaging device frame 208 has been adjusted. This leads to excellent maneuverability.

4) Eccentricity or swing of the imaging device frame 208 derived from a backlash can be suppressed without use of an elastic member.

The present invention is not limited to the aforesaid embodiments. Needless to say, embodiments constructed by combining parts of the embodiments will belong to the present invention.

Generally, in medical fields, there is a demand for imaging units that match endoscopes to be used exclusively for different surgical procedures. The imaging units are different from one another in terms of an attachment that is used to attach an imaging unit to the eyepiece unit of an endoscope, or in terms of a power offered by an optical system or inclusion of various filters or any other required mechanism. As one of means for coping with the demand, an imaging unit is divided into a camera head in which an imaging device is incorporated and a camera adaptor in which an image formation optical system is incorporated. The relatively expensive one of the camera head and camera adaptor is made available in a limited number of types and has common specifications. The relatively inexpensive one thereof is made available in a large number of types and has specifications specialized in each surgical procedure. A selected one of relatively expensive apparatus is combined with various types of relatively inexpensive apparatuses, whereby an imaging unit usable for various surgical procedures is realized. In this case, a user needs a variety of types of apparatuses specialized in a variety of surgical procedures. Therefore, theses apparatuses should be as inexpensive as possible.

For example, Japanese Unexamined Patent Publication No. 10-023597 has proposed an imaging unit for endoscopes that comprises a camera adaptor and a camera head that are separated apparatuses. An image formation optical system is incorporated in the camera adaptor, while an imaging device is incorporated in the camera head. Moreover, a focusing mechanism, an eccentricity adjusting mechanism, and other mechanisms for adjusting an optical system is included in the imaging unit.

In the imaging unit for endoscopes proposed in the Japanese Unexamined Patent Publication No. 10-023597, the camera adaptor and camera head that can be detached from each other resist autoclaving and include the eccentricity adjusting mechanism and focusing mechanism respectively. However, one of the two mechanisms is incorporated in the camera adaptor, and the other mechanism is incorporated in the camera head. Namely, the mechanisms that cost a lot are distributed to the camera adaptor and camera head. Therefore, both the camera adaptor and camera head are expensive.

In contrast, an imaging unit for endoscopes proposed in Japanese Unexamined Patent Publication No. 09-066725 includes a camera adaptor in which electric circuits are incorporated and a camera head in which an imaging device is incorporated. The camera adaptor and camera head can be separated from each other while being kept hermetic to resist autoclaving. A signal is transferred between the camera adaptor and camera head through a connector.

In the imaging unit for endoscopes proposed in the Japanese Unexamined Patent Publication No. 09-066725, the imaging unit resists autoclaving and includes a focusing mechanism. However, the imaging unit does not include an eccentricity adjusting mechanism, and has therefore the fear that an endoscopic image may be eccentric. Supposing a mechanism is included for moving an image formation optical system, which is stowed in a hermetic frame, in a direction perpendicular to the optical axis thereof, the hermetic frame has a path linking the interior of the hermetic frame and the exterior thereof. It is therefore hard to keep the hermetic frame perfectly hermetic.

(Object)

An object of the present embodiment is to provide an imaging unit for endoscopes that resists autoclaving and includes a camera head and a camera adaptor. Herein, either of the camera head and camera adaptor that must be available in diverse types is inexpensive. Moreover, the camera adaptor including electric circuits and the camera head including an imaging device can be separated from each other. A signal is transferred between the camera adaptor and camera head through a connector. Moreover, production of an eccentric image can be prevented.

Figure 10:
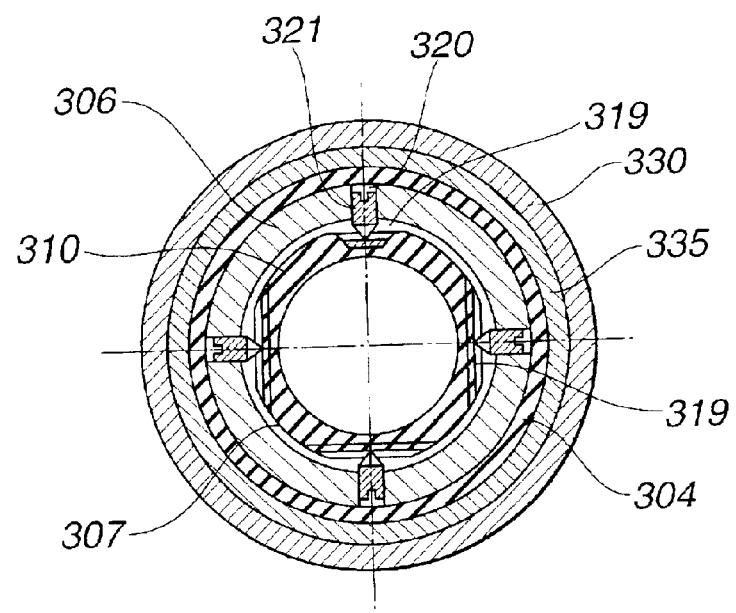
FIG. 10 is a X—X sectional view of the structure shown in FIG. 9.
Figure 9:
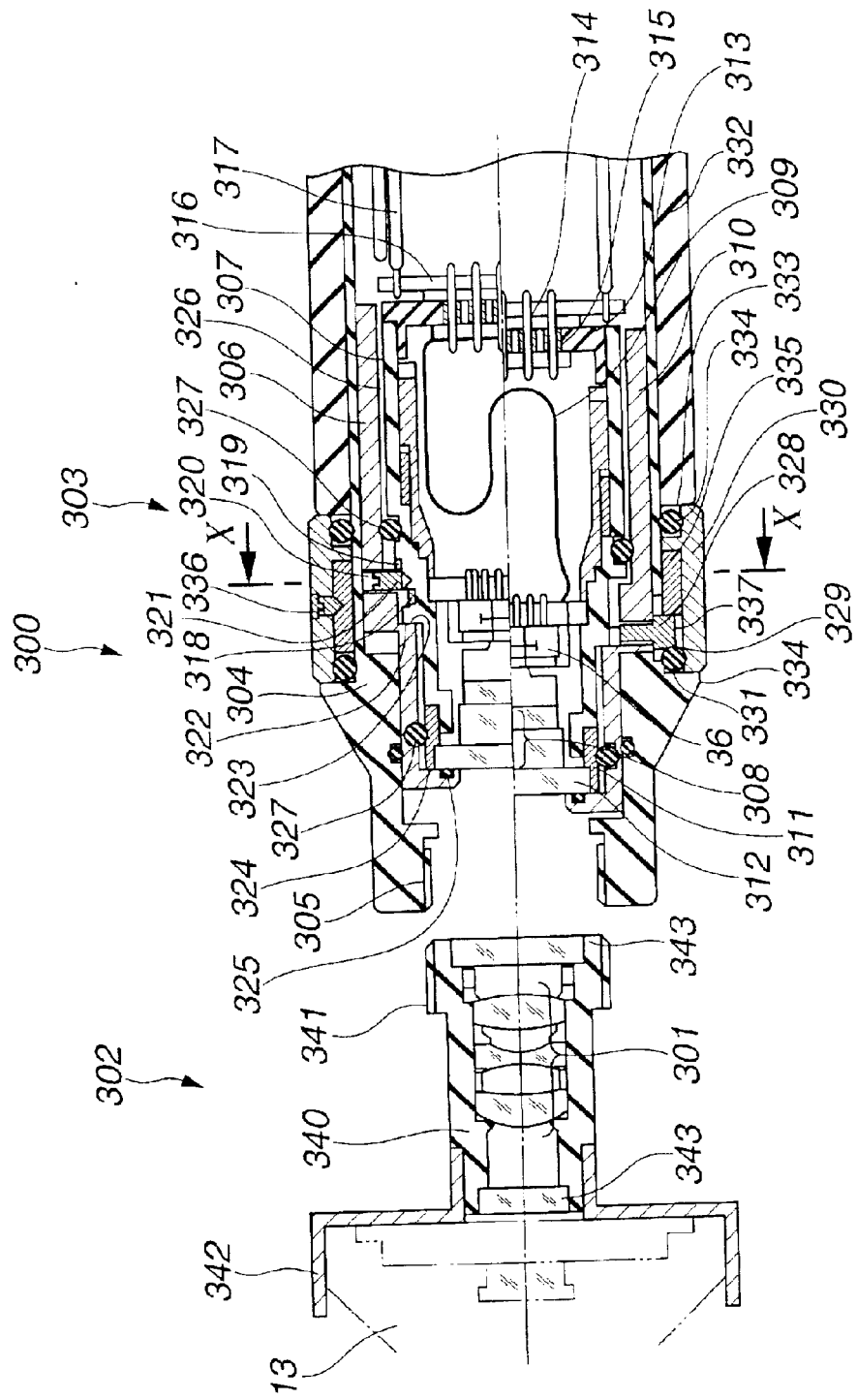
FIG. 9 is a sectional view showing the structure of an imaging unit for endoscopes (TV camera) according to a seventh embodiment.
Figure 11:
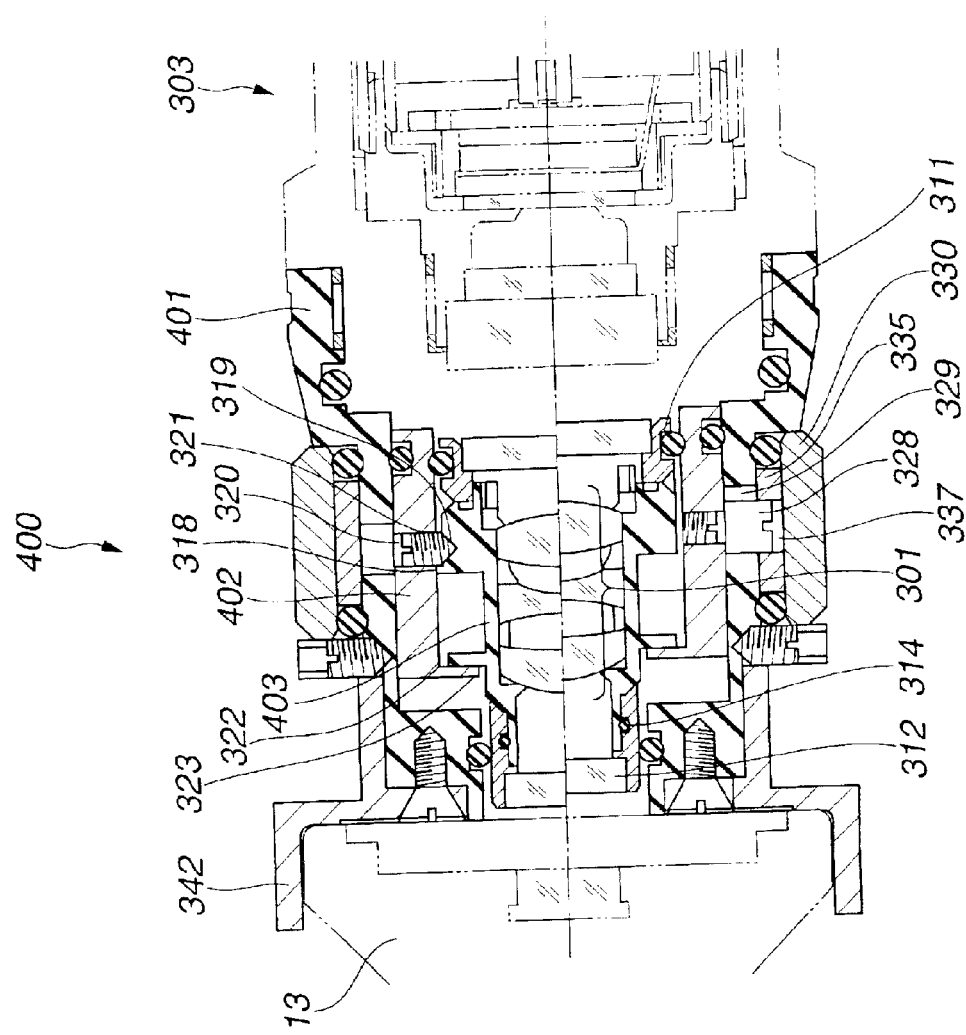
FIG. 11 is a sectional view showing the structure of a camera adaptor.
Figure 12:
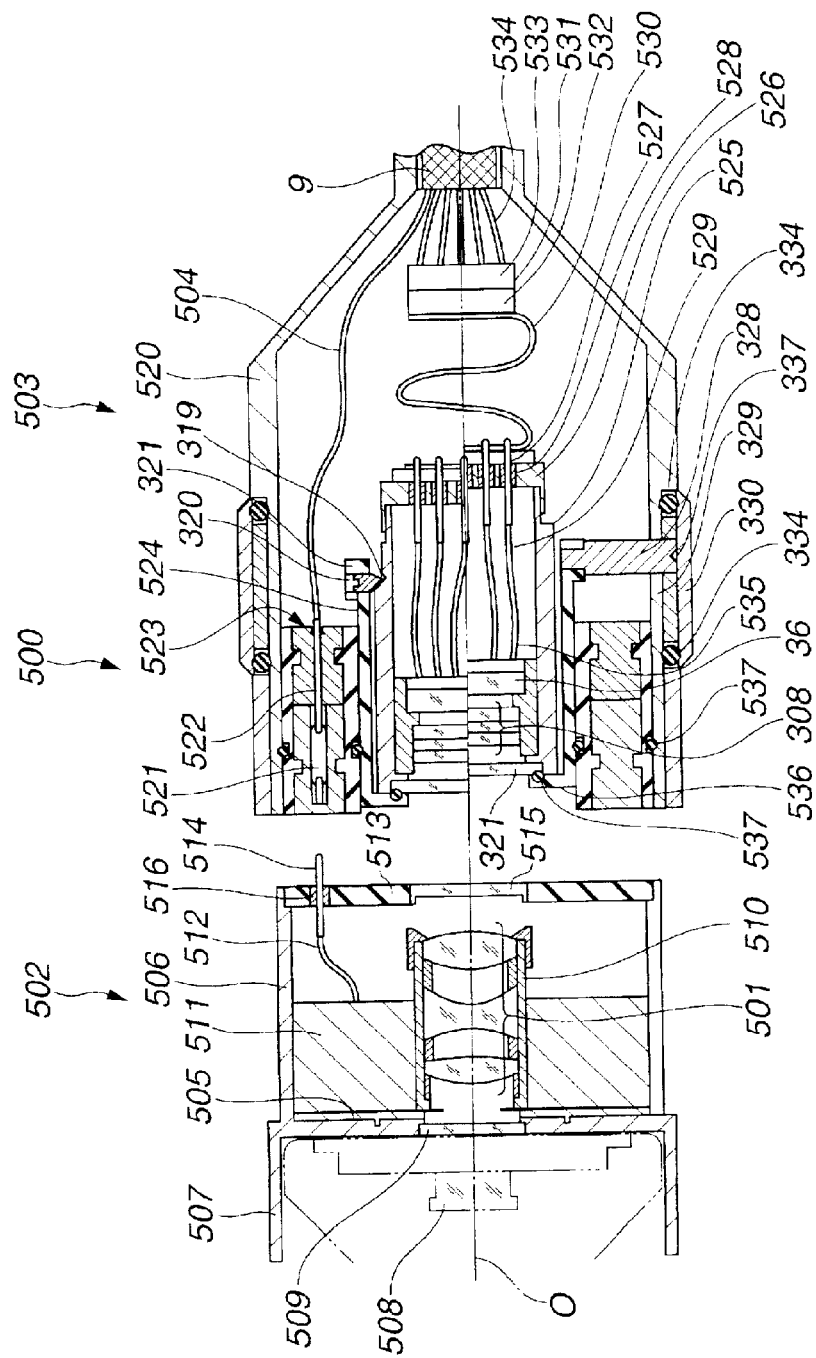
FIG. 12 is a sectional view showing the structure of an imaging unit for endoscopes (TV camera) in accordance with a modified example.

FIG. 9 is a sectional view showing the structure of an imaging unit for endoscopes (TV camera) in accordance with a seventh embodiment of the present invention. FIG. 10 is an X—X sectional view of the structure shown in FIG. 9. FIG. 11 is a sectional view showing the structure of a camera adaptor. FIG. 12 is a sectional view showing a variant of the imaging unit for endoscopes (TV camera). In FIG. 9, FIG. 11, and FIG. 12 alike, movable components are shown with the positions thereof differentiated between the upper and lower sections of each sectional view.

As shown in FIG. 9, a TV camera 300 that is the imaging unit for endoscopes comprises a camera adaptor 302 and a camera head 303. An image formation optical system 301 for forming an optical image propagated from the endoscope 2 is incorporated in the camera adaptor 302. The CCD 36 that is an imaging device for picking up the formed optical image and converting it into an electric signal is incorporated in the camera head 303. First, the structure of the camera head 303 will be described below.

A camera housing 304 that is a frame for the camera head 303 is hollowed and shaped substantially like a cylinder. A screw 305 with which the camera head is screwed to the camera adaptor 302 is threaded in the inner surface of the front part of the camera housing 304. A substantially cylindrical sleeve 306 is inserted in the camera housing 304 so that the sleeve 306 can slide along the optical axis of an optical system incorporated therein. A hermetic unit 307 in which the CCD 36 is incorporated is stowed in the sleeve 306. Aside from the CCD 36, a group of optical filters 308 and a flexible substrate 309 are enclosed in the hermetic unit 307.

A glass frame 311 is locked in the front end of a hermetic unit housing 310 that outlines the hermetic unit 307. The glass,frame 311 is locked hermetically by tightening screws that are brazed, welded, bonded, or sealed using a metal. A highly heat-resisting cover glass 312 made of sapphire or the like is hermetically locked in the glass frame 311 by performing brazing or the like. A lid member 313 is locked in the rear end of the hermetic unit housing 310 in order to block the opening of the rear end. The lid member 313 is hermetically locked in the hermetic unit housing 310 in the same manner as the glass frame 311 is. Consequently, the rear end of the hermetic unit 307 is hermetically sealed. Thus, the front end and rear end of the hermetic unit 307 are hermetically sealed, and the hermetic unit 307 is completed.

Contact pins 314 via which an electric signal produced by the CCD 36 is outputted to outside the hermetic unit 307 pierce through the lid member 313. Gaps created between the contact pins 314 and lid member 313 are hermetically sealed by sintering a vitreous material 315. The contact pins 314 are coupled to the flexible substrate 309 within the hermetic unit 307. A substrate 316 is located outside the hermetic unit 313 with a spacer therebetween. The contact pins 314 are coupled to the substrate 316, and a group of harnesses 317 is extended from the substrate 316 to the rear end of the camera head. The group of harnesses 317 extends from the rear end of the camera head 303 and forms the signal cable 9.

The hermetic unit 307 has two pairs of planar parts 318, that is, four planar parts 318 formed as parts of the outer circumference thereof. Each pair of planar parts 318 is opposed to each other with the optical axis as a center within a plane perpendicular to the optical axis. For example, referring to FIG. 10, a pair of planar parts 318 is formed as the upper and lower parts of the periphery of the hermetic unit, and another pair of planar parts 318 is formed as the left and right parts thereof. A V-shaped groove 319 shaped like letter V on a plane that contains the optical axis as a center thereof.

Among the V-shaped grooves 319 formed in the two pairs of opposed planar parts 318, one V-shaped groove 319 formed at the upper point on the plane perpendicular to the optical axis is shorter on the plane perpendicular to the optical axis than the other V-shaped groove 319. This is intended to use the V-shaped groove 319, which is formed at the upper point on the plane perpendicular to the optical axis, as an index that helps identify, for example, the up direction of the hermetic unit 307. Screw grooves 320 are formed at positions in the sleeve 306 coincident with the positions of the two pairs of opposed V-shaped grooves 319. Tapered adjustment screws 321 are meshed with the screw grooves 320, and pierce through the sleeve 306. The tips of the two pairs of opposed adjustment screws 321 that jut out from the inner surface of the sleeve 306 abut on the front parts of the inclined walls of the V-shaped grooves 319. The two pairs of opposed adjustment screws 321 are used to bear the hermetic unit 307. Consequently, the hermetic unit 307 is immobilized in directions of eccentricity.

A step portion whose diameter is smaller than the other part of the hermetic unit housing 310 is formed as a portion of the hermetic unit housing 310 beyond the V-shaped grooves 319 near the front end of the hermetic unit housing 310. An abutment surface 323 that abuts on an abutment surface 322 of the sleeve 306, which will be described later, is formed to face the front end of the hermetic unit housing 310. A step portion whose inner diameter is smaller than the other part of the sleeve 306 is formed as a portion of the sleeve 306 that has the rear end abutted on the abutment surface 323 and extends along the optical axis. The abutment surface 322 that abuts on the abutment surface 323 is formed as part of the inner surface of the step portion of the sleeve 306 that faces the rear end of the sleeve 306. Owing to the abutment surfaces 322 and 323, the hermetic unit 307 is hindered from moving towards the front end of the camera head. When the adjustment screws 321 are tightened, the adjustment screws 321 are pressed against the front parts of the walls of the V-shaped grooves 319. Consequently, the hermetic unit housing 310 has a portion thereof between the adjustment screws 321 and the abutment surface 322 clamped by the adjustment screws 321 and the abutment surface 322. Consequently, the position of the hermetic unit 307 along the optical axis is determined. The abutment surfaces 322 and 323 are surfaces substantially perpendicular to the optical axis. Even when the hermetic unit 307 is moved in a direction of eccentricity, the hermetic unit 307 will not tilt relative to the optical axis.

An inward facing flange 324 formed at the distal end of the sleeve 306 blocks a part of the front end of the hermetic unit 307. An O ring 325 is interposed between the rear end of the inward facing flange 324 and the hermetic unit 307. Consequently, even when the hermetic unit 307 is moved in a direction of eccentricity, the camera head is kept hermetic.

A movement space 326 permitting the hermetic unit 307 to move in a direction of eccentricity is created between the inner surface of the sleeve 306 and the outer circumference of the hermetic unit 307. Eccentricity can be adjusted within the range of the movement space 326. An O ring 327 is placed at a point near the front end of the hermetic unit 307 and at a point beyond the V-shaped grooves 319 a bit away from the rear end thereof on the outer circumference of the hermetic unit 307. Thus, the movement space 326 is kept watertight.

The two pairs of opposed adjustment screws 321 are each opposed to each other with the optical axis as a center on a plane perpendicular to the optical axis. For convenience's sake, one of the pairs of adjustment screws 321 shall be referred to as a first pair, and the other pair shall be referred to as a second pair. Moreover, a direction defined with a line linking the two adjustment screws 321 that belong to the first pair shall be referred to as a first direction. A direction defined with a line linking the two adjustment screws 321 that belong to the second pair shall be referred to as the second direction.

The adjustment screws 321 are arranged such that the first direction and second direction will be orthogonal to each other. Once the two adjustment screws 321 belonging to the first pair are loosened to such an extent that no gap will be created between the hermetic unit 307 and sleeve 306, the hermetic unit 307 can be moved in the second direction by loosening one of the adjustment screws 321 that belong to the second pair and tightening the other adjustment screw. Likewise, the hermetic unit 307 can be moved in the first direction. As mentioned above, the position in a direction of eccentricity of the hermetic unit 307 relative to the sleeve 306 can be adjusted owing to the adjustment screws 321 piercing through the sleeve 306 and the V-shaped grooves 319 formed in the hermetic unit 307.

Aside from the adjustment screws 321, a cam pin 328 is fixed to the outer circumference of the sleeve 306. A first cam groove 329 is formed in the camera housing 304 to extend along the optical axis. The first cam groove 329 is used to forcibly guide the cam pin 328. The cam pin 328 pieces through the first cam groove 329 and juts outside the camera housing 304.

A focus ring 330 is mounted on the outer circumference of the camera housing 304 so that the focus ring 330 can be turned. The focus ring 330 has the ends thereof opposed to a hit surface 331 of the camera housing 304 and to a front-end surface 333 of a housing cover 332 that covers the outer circumference of the camera housing 304 with a minute gap therebetween. The focus ring 330 is thus prevented from moving in longitudinal directions of the camera head. Moreover, an O ring 334 is interposed between the inner surface of the focus ring 330 and the outer circumference of the camera housing 304 in order to thus keep the camera housing 304 watertight. Another ring 335 is stowed inside the focus ring 330. The focus ring 330 is fixed to the ring 335 using a fixation screw 336 piercing through the focus ring 330.

The ring 335 has a spirally shaped second cam groove 337 formed therein. The cam pin 328 that pierces through the first cam groove 329 formed in the camera housing 304 and juts out is fitted into the second cam groove 337.

When the focus ring 330 is turned, force is applied to the cam pin 328 because of the second cam groove 337 formed in the ring. since the second cam groove 337 is spirally shaped, the force is dispersed in a circumferential direction in which the focus ring 330 is turned and in the longitudinal directions of the camera head. However, since the cam pin 328 is hindered from rotating by the first cam groove 329, the cam pin 328 is forced to move in a longitudinal direction. This causes the hermetic unit 307 to move in an optical-axis direction. Consequently, the camera head is focused.

Next, the camera adaptor 302 will be described below.

An adaptor housing 340 that is a frame of the camera adaptor 302 is hollowed and shaped substantially like a cylinder. A screw 341 with which the camera adaptor is screwed to the camera head 303 is threaded on the outer circumference of the rear part of the adaptor housing 340. A mount 342 enabling attachment of the endoscope 2, in which a unique eyepiece unit is incorporated, is integrated with the front part of the camera adaptor 302. An image formation optical system 301 composed of a plurality of lenses is, as mentioned previously, stowed in the camera adaptor 340. The adaptor housing 340 is equivalent to the hermetic unit 307 incorporated in the camera head 303. A cover glass 343 is hermetically locked in the openings of both the ends of the adaptor housing 340 using the same means as the means adopted for the hermetic unit 307.

After the TV camera 300 has the foregoing components thereof assembled, the TV camera 300 is attached to the eyepiece unit 13 of the endoscope. The endoscope 2 is now usable.

First, the camera adaptor 302 and camera head 303 are joined with the screw 341 meshed with the screw 305 in order to construct the TV camera 300. The TV camera 300 is then attached to the eyepiece unit 13 of the endoscope 2 with the mount 342 joined to the eyepiece unit 13. The signal cable 9 is plugged in to the CCU 5. The endoscope is activated, and a picture of an object is displayed on the monitor 6.

If the position of the picture of the object displayed on the monitor 6 is deviated from a right position, if the picture lacks any image, or if an image is eccentric, the hermetic unit 307 incorporated in the camera head 303 has eccentricity thereof adjusted.

First, the first pair of adjustment screws 321 is loosened to such an extent that a gap is created little between the hermetic unit 307 and sleeve 306. Once the first pair of adjustment screws 321 is loosened, the hermetic unit 307 can be moved in the second direction using the second pair of adjustment screws 321. One of the second pair of adjustment screws 321 is loosened and the other one is tightened, whereby a position at which the hermetic unit 307 is secured is adjusted in terms of the second direction. At this time, since the first pair of adjustment screws 321 is loosened to such an extend that a gap is little created between the hermetic unit 307 and sleeve 306, the position at which the hermetic unit 307 is secured is hardly deviated from a right position in terms of the first direction. Thereafter, the first pair of adjustment screws 321 is manipulated in the same manner as the second pair of adjustment screws 321 was, and the second pair of adjustment screws 321 is manipulated in the same manner as the first pair of adjustment screws 321 was. Consequently, the position at which the hermetic unit 307 is secured can be adjusted in terms of the first direction. Thus, the position at which the hermetic unit 307 is secured is adjusted by alternating the first direction and second direction that are orthogonal to each other on the plane perpendicular to the optical axis. Consequently, the hermetic unit 307 is moved in directions of eccentricity in order to adjust the position at which the hermetic unit 307 is secured. By performing the foregoing manipulations, eccentricity of an optical image displayed on the monitor 6 is nullified.

Moreover, it a picture displayed on the monitor 6 is out of focus, the focus ring 330 is turned for the purpose of focusing. When the focus ring 330 is turned, the second cam groove 337 formed in the ring 335 fixed as an integral part of the focus ring 330 to the focus ring 330 is rotated. Consequently, the cam pin 328 piercing through the first cam groove 329 formed in the camera housing 304 is forced to move in an optical-axis direction. This causes the hermetic unit 307 to which the cam pin 328 is fixed to move in the optical-axis direction. The CCD 36 enclosed in the hermetic unit 307 then moves in the optical-axis direction. Consequently, focusing is achieved. The picture of the object displayed on the monitor 6 is no longer out of focus.

As mentioned above, the eccentricity adjusting mechanism and focusing mechanism are incorporated in the camera head 303. No adjusting mechanism need be incorporated in the camera adaptor 3Q2. The camera adaptor 302 can be manufactured inexpensively. Moreover, various types of camera adaptors 302 that are different from one anther in terms of a power offered by lenses or a mechanism enabling attachment to an endoscope can be manufactured inexpensively. This results in an endoscope system adaptable to various surgical procedures performed in medical fields. Furthermore, the hermetic unit 307 in the camera head 303 serves as the focusing mechanism that will not rotate but can move only in optical-axis directions. Therefore, a picture representing an optical image will not be turned but can be adjusted successfully.

Next, a variant in which the structure enabling adjustment of eccentricity and focusing is incorporated in the camera adaptor 302 but not in the camera head 303 unlike as described referring to FIG. 9 will be described referring to FIG. 11.

A camera adaptor 400 has an adaptor housing 401 as a frame thereof. The adaptor housing 401 is hollowed and shaped substantially like a cylinder. A substantially cylindrical sleeve 402 is inserted inside the adaptor housing 401 so that the sleeve 402 can slide along the optical axis of an optical system incorporated in the camera adaptor. A hermetic unit 403 having an image formation optical system 301 incorporated therein is stowed in the sleeve 402. The hermetic structure of the hermetic unit 403, and the structure for placing the hermetic unit 403 at a position so that the position can be adjusted in a direction perpendicular to the optical axis are identical to those described referring to FIG. 9.

After the TV camera has the foregoing components thereof assembled, the TV camera is attached to the eyepiece unit 13 of the endoscope. The endoscope 2 is now usable.

The position of a picture of an object displayed on the monitor may be deviated from a right position, the picture may lack any image, an image may be eccentric, or focusing may anyhow be needed. In this case, the hermetic unit 403 having the image formation optical system 301 incorporated therein is moved in a direction perpendicular to the optical axis, and then secured. The procedure is identical to that described referring to FIG. 9.

Consequently, the present variant provides the same advantages as the TV camera 300 described referring to FIG. 9. In addition, since both the eccentricity adjusting mechanism and focusing mechanism are incorporated in the camera adaptor 400, any adjusting mechanism need not be included in the camera head 303. The camera head 303 can therefore be manufactured inexpensively. Moreover, various types of camera heads that are different from one another in terms of an optical filter incorporated, an appearance, or various switches used to remotely control peripheral equipment can be manufactured inexpensively. This results in an endoscope system adaptable to various surgical procedures performed in medical fields.

Next, an imaging unit for endoscopes whose camera adaptor and camera head are identical to the camera adaptor 302 of the TV camera 300 and the camera head 303 thereof respectively, which are described referring to FIG. 9, will be described referring to FIG. 12. The camera adaptor 302 includes electric circuits. Herein, a signal is transferred and received between the camera adaptor and camera head through connectors, and eccentricity of an image can be avoided.

A TV camera 500 that is the imaging unit for endoscopes consists mainly of a camera adaptor 502 and a camera head 503 similarly to the TV camera described referring to FIG. 9. An image formation optical system 501 for forming an optical image propagated from the endoscope 2 is incorporated in the camera adaptor 502. The CCD 36 that is an imaging device for picking up the formed optical image and converting it into an electric signal is incorporated in the camera head 503. Thus, an optical image picked up by the endoscope 2 is visualized. The TV camera 500 is different from the TV camera 300 described referring to FIG. 9 in the points described below.

The CCU 5 generates a driving signal that represents an average level of luminance and is used to adjust brightness. The driving signal is transmitted to the camera head 503 over the signal cable 9. The driving signal is applied to an iris drive unit 511 stowed in the camera adaptor 502 over a harness 504 lying in the camera head 503. Consequently, the size of an aperture stop defined by aperture blades 505 included in the iris drive unit 511 is varied in order to adjust an amount of light coming from the endoscope 2. Thus, brightness is automatically adjusted in order to provide an optical image of proper brightness.

A mount 507 to which the endoscope 2 is fixed is formed at the front end of a substantially cylindrical adaptor housing 506 that outlines the camera adaptor 502. A first cover glass 509 is hermetically locked in an opening that is opposed to an eyepiece window 508 formed in the eyepiece unit of the endoscope 2 and centered on the optical axis O of an optical system incorporated in the camera adaptor. A lens frame 510 accommodating an image formation optical system 501 is placed in the adaptor housing 506, which is hermetically sealed using the first cover glass 509, with the center of the lens frame 510 aligned with the optical axis O.

Moreover, the ring-like iris drive unit 511 is mounted on the outer circumference of the lens frame 510 within the adaptor housing 506. When a driving signal is applied to a drive motor (not shown) incorporated in the iris drive unit 511, the size of an aperture stop defined by the aperture blades 505 is varied in order to adjust an amount of light incident on the image formation optical system 501. One ends of harnesses 512 are coupled to the iris drive unit 511, and the other ends thereof are fastened to contact pins 514 fixed to a first plug 513 that is hermetically locked in the rear end of the adaptor housing 506.

The first plug 513 is concentric with a second cover glass 515 hermetically locked in the circular opening of the rear end of the adaptor housing 506. The plurality of contact pins 514 is fixed to the annular portion around the second cover glass 515, and kept hermetically using a vitreous hermetic seal 516. Namely, the contact pins 514 are passed through bores whose diameter is larger than the diameter of the contact pins 514. A fused glass is poured into the bores in which the contact pins are fitted, whereby the vitreous hernetic seal 516 is formed. As mentioned above, the center of the rear end of the adaptor housing 506 is formed as an optical path, and surrounded with the contact pins 514. This leads to the small outer diameter of the camera adaptor 502.

On the other hand, a camera housing 520 outlining the camera head 503 is shaped like a cylinder that is tapered backwards. A first receptacle 523 shaped substantially line a cylinder and composed of a socket 521 and a contact pin 522 is fitted in the camera housing 520.

A substantially cylindrical sleeve 524 is inserted in the first receptacle 523 so that the sleeve can slide along the optical axis of an optical system incorporated in the camera housing. A hermetic unit 525 in which the CCD 36 and others are incorporated is stowed in the sleeve 524. The structures of the sleeve 524 and hermetic unit 525 are identical to those described referring to FIG. 9.

Moreover, a third metallic plug 526 is hermetically locked in the opening of the rear end of the hermetic unit 525. Contact pins 527 are hermetically fixed to the third plug 526 using a vitreous hermetic seal 528 so that the contact pins 527 will juts inwards and outwards the third plug 526. Within the hermetic unit 525, the contact pins 527 and leads 535 jutted out of the back of the CCD 36 are linked by harnesses 529. Outside the hermetic unit 525, a flexible substrate 530 is coupled to the contact pins 527 jutted out of the hermetic unit 525, and to a connector 531. The connector 531 consists of a second plug 532 and a second receptacle 533. The rear end of the second receptacle 533 is coupled to harnesses 534 that constitute the cable 9.

Moreover, the contact pin 522 fixed to the rear end of the first receptacle 523 and the signal cable 9 are linked by the harness 504. When the camera adaptor 502 is joined to the camera head, an iris driving signal is transferred to the iris drive unit 511 via the first receptacle and first plug. An O ring 537 is interposed between the outer circumference of the sleeve 524 and the inner surface of the first receptacle 523, between the outer surface of the first receptacle 523 and the inner surface of the camera housing 520, and between a flange 536 formed at the front end of the sleeve 524 and the front end of the hermetic unit 525. Thus, the camera housing 520 is kept watertight.

After the TV camera 500 has the foregoing components thereof assembled, the TV camera 500 is attached to the eyepiece unit 13 of the endoscope. The endoscope 2 is now usable.

The position of a picture of an object displayed on the monitor 6 may be deviated from a right position, the picture may lack any image, an image may be eccentric, or focusing may anyhow needed. In this case, the same procedure as the procedure described referring to FIG. 9 is carried out.

Consequently, the TV camera 500 provides the same advantages as the TV camera 300 that is an imaging unit for endoscopes and described referring to FIG. 9. In addition, since the camera adaptor 502 includes neither a focusing mechanism nor an eccentricity adjusting mechanism, and the adaptor housing 506 need not have a path linking the exterior and interior of the adaptor housing, the TV camera 500 can be kept so hermetic as to be autoclaved. Moreover, while the camera adaptor 502 and camera head 503 are kept so hermetic as to be autoclaved, they can transfer or relay an electric signal. Moreover, the center of the camera adaptor 502 is formed as an optical path, and surrounded with the contact pins. This results in the camera adaptor 502 having a small outer diameter. Even in the camera head 503, the hermetic unit 525 in which the imaging optical system 501 is stowed in the center thereof, and a mechanism for adjusting eccentricity of the hermetic unit 525 can slide on the inner surface of the first receptacle 523. This results in the camera head 503 having a small outer diameter.

Figure 13:
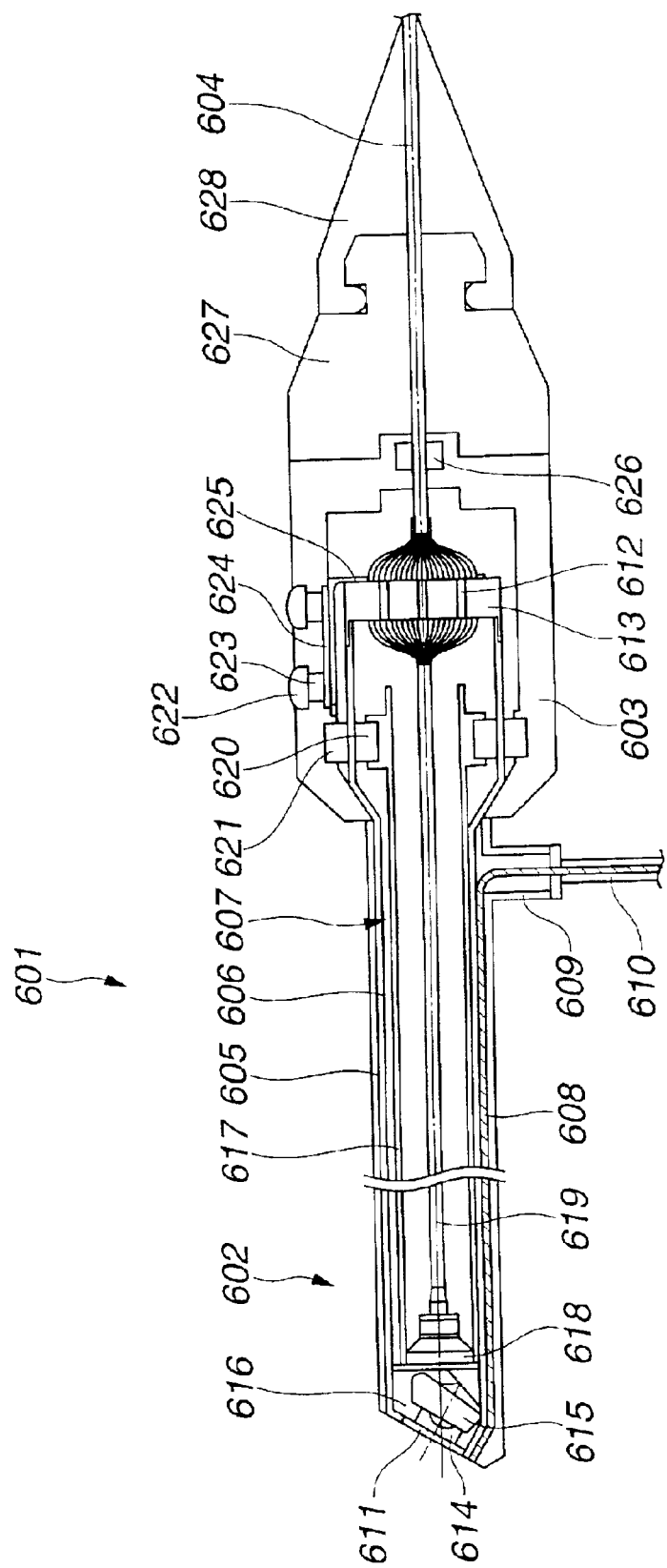
FIG. 13 is a sectional view for explaining an imaging unit for endoscopes according to an eighth embodiment.

FIG. 13 shows an eighth embodiment.

The present embodiment provides an imaging unit for endoscopes into which the endoscope 2 and the imaging unit 3 for endoscopes of the first embodiment are integrated. The apparatuses connected to the imaging unit for endoscopes are identical to those connected to the imaging unit for endoscopes of the first embodiment.

As a background of the present embodiment, problems underlying the present invention will be described below.

An electronic endoscope having a solid-state imaging device such as a CCD incorporated in the distal part of an insertion member of the endoscope has been realized based on a known art. When it comes to a rigid endoscope employed in surgery, a viewing direction defined by an objective optical system incorporated in the distal part of an insertion member meets the axial direction of the insertion member at a certain angle, for example, 30°, 70°, or 90°. Conventionally, an operator using an endoscope that offers such a viewing direction turns the insertion member to pick up required images. At this time, when a solid-state imaging device rotates together with an objective optical system, the positional relationship of the operator to a monitor is broken with every rotation of the solid-state imaging device. The operator may not be able to correctly orient the distal part of the insertion member.

Therefore, a rotating mechanism is usually interposed between the objective optical system and solid-state imaging device. Otherwise, an image to be displayed on the monitor is rotated through image processing, or the monitor itself is rotated.

However, an endoscope and a camera head that is included in an imaging unit for endoscopes and has a solid-state imaging device incorporated therein may be separated from each other as described in relation to the first embodiment. Incidentally, an endoscope having an endoscope and a camera head as separated apparatuses has been a mainstream in the past. An operator using this type of endoscope system recognizes the up direction of the solid-state imaging device as the up direction of the camera head.

For example, referring to FIG. 13, switches serve as an index of the up direction. Namely, the up direction of the solid-state imaging device must be agreed with the up direction of the camera head.

An endoscope system used to perform surgery must be able to be sterilized as described in relation to the first embodiment. AS mentioned previously, an optical system must have a hermetic structure that does not permit invasion of steam so as to prevent condensation. When a solid-state imaging device is incorporated in the distal part of an insertion member, the solid-state imaging device must be placed in a hermetic space. At this time, the solid-state imaging device must be rotated with respect to an objective optical system without coming into mechanical contact with any structure. At the same time, the position of the solid-state imaging device relative to the casing of a camera head must be held unchanged. Supposing the solid-state imaging device is rotated using a motor placed in the hermetic space, a means for adjusting the position of the solid-state imaging device relative to the camera head is needed separately. If an insertion member having an outer diameter of 4 mm is realized with an imaging unit for endoscopes, the imaging unit becomes large in size, structurally complex, and hard to manipulate. This leads to an increase in the costs of manufacturing.

The foregoing problems can be solved with the embodiment described below.

Differences of an eighth embodiment from the first embodiment will be solely described referring to FIG. 13 below.

FIG. 13 is a sectional view conceptually showing an imaging unit for endoscopes of the present invention.

An imaging unit for endoscopes 601 is divided broadly into an insertion member 602, a hand-held unit 603, and a cable 604 in terms of appearance. The insertion member 602 is sheathed with an armor 605. A hermetic frame 606 is placed inside the inner surface of the armor 605. A portion of the hermetic frame 606 and a portion of the armor 605 that are in contact with each other are welded to be a welded portion 607. The inner diameter of the armor 605 is different from the outer diameter of the hermetic frame 606. A light guide 608 realized with an optical fiber is inserted in a gap between the armor 605 and hermetic frame 606. The light guide 608 is jutted outwards as a light guide cable 610 through a base 609, and plugged in to a light source apparatus (not shown).

A cover window 611 is hermetically joined to the distal end of the hermetic frame 606 by performing soldering. A hermetic connector 613 is hermetically locked in the opposite end of the hermetic frame 606 within the hand-held unit 603. The hermetic connector 613 is composed of contact pins 612 that are hermetically joined by applying a vitreous material to the peripheries thereof and that provide electric contacts. An objective optical system 616 including an image formation lens 614 and a prism unit 615 is placed inside the cover window 611. A CCD frame 617 that can rotate about the longitudinal axis of the insertion member 602 with respect to the hermetic frame 606 is placed inside the hermetic frame 606. A CCD 618 is incorporated in the CCD frame 617 in the distal part of the insertion member at a predetermined distance from the objective optical system 616 at a predetermined angle with respect to the objective optical system 616. A signal line 619 is extended from the CCD 618 while electrically coupled to the CCD 618. The signal line 619 includes a drive circuit incorporated in the insertion member, runs through the insertion member, and reaches the contact pins 612 of the hermetic connector 613.

A plurality of magnets A 620 made of a rare earth metal or alloy, such as, neodymium magnets or samarium-cobalt magnets is fixed to the outer circumference side the CCD frame 617 in the interior of the hand-held unit. Magnets B 621 made of the same material as the magnets A are secured within the hand-held unit 603 while being paired with the magnets A with the hermetic frame 606 therebetween. The magnets B are magnetically coupled to the magnets A 620 while being in noncontact with the magnets A.

A switch button 622 serving as an index of the up direction of the imaging unit for endoscopes 601 is exposed on the periphery of the hand-held unit 603. A switch base substrate 624 on which a switch 623 is mounted is secured inside the switch button within the hand-held unit 603. The switch 623 is electrically connected to the contact pins 612 of the hermetic connector 613 by ways of a flexible substrate 625 extending from the switch base substrate 624 or a harness.

An end of a cable 604 is coupled to the contact pins 612 outside the hermetic connector 613. A gap between the cable 604 and hand-held unit 603 is kept watertight owing to a sealing member 626 realized with an elastic member. A hand-held unit casing member 627 is fixed to the end of the hand-held unit 603 from which the cable 604 is jutted out. An anti-breakage member 628 is fixed to the hand-held unit casing member 627.

In addition to the foregoing components, a slip ring that is not shown may be placed ahead of and behind the hermetic connector 613 so that the signal line 619 or cable 604 and the hermetic connector 613 can be freely rotated relative to each other. Moreover, if the cable 604 is permitted to rotate during use of the imaging unit, the slip ring may be solely interposed between the signal line 619 and hermetic connector 613.

Moreover, the up direction of the hand-held unit 603 may be clearly expressed by devising the shape of the hand-held unit 603 or creating a concave or convex part of the hand-held unit 603 instead of using the switch 623.

An operation to be exerted by the present embodiment will be described below. The same operations as those exerted by the aforesaid embodiments will not be described.

An image of an object illuminated by light propagated over the light guide cable is passed through the cover window, and converged on the CCD through the objective optical system. The CCD performs photoelectric conversion. Consequently, the image signal is converted into an electric signal, transmitted over the signal line, and applied to a CCU (not shown) via the hermetic connector over the cable.

For obtaining a desired field of view, an operator must change the viewing direction (direction of arrow A in the drawing) offered by the objective optical system incorporated in the distal part of the insertion member with respect to the axis of the insertion member. The operator rests his/her finger on the base of the light guide cable while holding the hand-held unit, and pushes the base to turn it. This causes the armor and hermetic frame to rotate with respect to the hand-held unit. Consequently, the viewing direction offered by the objective optical system changes. At this time, the positions of the CCD frame and CCD relative to the hand-held unit remain unchanged (in the up direction) irrespective of the rotation of the hermetic frame. This is attributable to the magnetic coupling between the magnets placed on the outer circumference of the CCD frame and the magnets secured in the hand-held unit.

The up direction of the hand-held unit is sensed with an operator's hand or finger that touches the switch without the necessity of visual confirmation.

1) According to the present embodiment, an objective optical system rotating mechanism can be constructed for an endoscope that has a CCD incorporated in the distal part of an insertion member. Herein, the endoscope can be manipulated in the same manner as a conventional endoscope that is familiar to an operator and has a camera head as a separate apparatus. Namely, the operator can orient the CCD in its up direction by orienting a hand-held unit in its up direction. In other words, the objective optical system alone can be rotated with the up direction of the CCD agreed with the up direction of the hand-held unit.

2) Since the CCD is incorporated in the distal part of the insertion member, drawbacks occurring when an endoscope is attached to or detached from a camera head or the like can be overcome (a drawback that the endoscope may drop, a drawback that the endoscope has to be attached to or detached from the camera head or the like, or a drawback that a coupler may be dimmed). Consequently, there is provided an imaging unit for endoscopes capable of offering high image quality while being unaffected by a loss in an amount of light caused by a relay optical system or by a distortion. Moreover, the imaging unit for endoscopes is highly durable but will not suffer from breakage of any lens.

3) The endoscope has the CCD incorporated in the distal part of the insertion member and includes an objective optical system rotating mechanism, and is kept hermetic. The endoscope can therefore be autoclaved.

4) If a slip ring is used, an angle of rotation need not be restricted.

5) The up direction of the hand-held unit can be confirmed with a sensation received through a hand.

6) Since the CCD rotates with respect to the hand-held unit, the following two advantages are provided:

a) A time lag deriving from inclusion of an automatically correcting mechanism will not occur.

b) The up direction of the CCD is agreed with the up direction of the hand-held unit. An operator being familiarized with a conventional endoscope will not misapprehend the orientation of the CCD because of automatic correction.

The present invention is not limited to the aforesaid embodiments. For example, in the camera head shown in FIG. 5, FIG. 9, or FIG. 12, similarly to the camera head shown in FIG. 8, the imaging surface of the imaging device may be located in or near the middle of the engagement length of the device frame that can freely move in optical-axis directions in order to enable focusing.

As described so far, according to the present invention, the position of an imaging device relative to optical elements can be adjusted with a seal member, which is structured hermetically in order to reliably prevent invasion of steam generated during autoclaving, kept hermetic.

What is claimed is:

1. An imaging unit for endoscopes comprising:

optical elements for forming an optical image;

an imaging device for photoelectrically converting the optical image formed by the optical elements;

a cylindrical hollow member for holding the imaging device, the cylindrical hollow member forming a camera assembly;

a case for hermetically storing the optical elements and the camera assembly;

a fixing member provided at a predetermined position in the case for fixing the optical elements;

an inner ring provided with a helical cam groove, the inner ring being rotatably provided in the case;

an outer ring movable by a user to rotate around the case;

a magnet for magnetically coupling the inner ring and the outer ring via the case, the magnet driving the inner ring in accordance with the operation of the outer ring;

a rectilinear groove formed in the case along an optical axis of the optical elements;

a cam pin provided in the outer peripheral surface of the hollow member, which engages the helical cam groove and the rectilinear groove and moves along the rectilinear groove as the inner ring rotates;

wherein the rectilinear groove restricts the movement of the cam pin in a rotating direction and guides the camera assembly in advancing and withdrawing directions with respect to the optical elements; and an elastic member interposed between the front end of the cylindrical hollow member for holding the imaging device and an inner side of a front end of the case for hermetically storing the optical elements and the camera assembly such that backlash of the cylindrical hollow member is minimized.

2. An imaging unit for endoscopes according to claim 1, further comprising a movable member providing in the hollow member, the movable member moving in a direction crossing the optical axis of the optical elements, the movable member moving the imaging device by pushing the imaging device to adjust eccentricity of the imaging device relative to the optical axis of the optical elements.

3. An imaging unit for endoscopes according to claim 1, wherein an imaging surface of said imaging device is located substantially in a middle of an engagement length of a frame which holds said imaging device, the engagement length being in the direction of the optical axis.

* * * * *